US012646598B2

(12) United States Patent
Umlauft et al.

(10) Patent No.: US 12,646,598 B2
(45) Date of Patent: **\*Jun. 2, 2026**

(54) SYSTEMS AND METHODS FOR LONGITUDINAL TIMELINE PRESENTATION AND PREDICTIVE CLINICAL DECISION SUPPORT

(71) Applicant: GE Precision Healthcare LLC, Waukesha, WI (US)

(72) Inventors: Debra Umlauft, Slinger, WI (US); Attila Vojtek, Budapest (HU); Levente Árpád, Békéscsaba (HU); Monica Masini, Aldershot (GB); Kirsten Nehf, Waukesha, WI (US)

(73) Assignee: GE PRECISION HEALTHCARE LLC, Waukesha, WI (US)

( \* ) Notice: Subject to any disclaimer, the term of this patent is extended or adjusted under 35 U.S.C. 154(b) by 272 days.

This patent is subject to a terminal disclaimer.

(21) Appl. No.: 18/455,468

(22) Filed: Aug. 24, 2023

(65) Prior Publication Data

US 2025/0069713 A1     Feb. 27, 2025

(51) Int. Cl.
*G16H 10/60* (2018.01)
*G06F 3/0482* (2013.01)
*G06F 3/04847* (2022.01)

(52) U.S. Cl.
CPC ........... *G16H 10/60* (2018.01); *G06F 3/0482* (2013.01); *G06F 3/04847* (2013.01)

(58) Field of Classification Search
None
See application file for complete search history.

(56) References Cited

U.S. PATENT DOCUMENTS 8,496,594 B2    7/2013  Taylor et al.
9,888,968 B2    2/2018  Sauer et al.
(Continued)

FOREIGN PATENT DOCUMENTS

WO     WO-2022256041 A1 * 12/2022  ............. G16H 30/20
WO     WO-2023220534 A1 * 11/2023  ........... G06T 11/206

OTHER PUBLICATIONS

A. A. T. Bui, D. R. Aberle and H. Kangarloo, "TimeLine: Visualizing Integrated Patient Records," in IEEE Transactions on Information Technology in Biomedicine, vol. 11, No. 4, pp. 462-473, Jul. 2007, doi: 10.1109/TITB.2006.884365. (Year: 2007).*

(Continued)

*Primary Examiner* — Emily Huynh
(74) *Attorney, Agent, or Firm* — McCoy Russell LLP

(57)          ABSTRACT
Various methods and systems are provided for a longitudinal patient history timeline and predictive clinical decision support system. In one example, a computing device comprising a display screen displays a menu listing one or more electronic medical records (EMRs) of one or more patients, and additionally is configured to display a patient timeline graphical user interface (GUI) accessible from the menu while the one or more EMR systems are in an un-launched state. The patient timeline GUI displays patient data as longitudinal medical history event elements and includes elements representing predicted outcomes generated by one or more artificial intelligence (AI) algorithms based on the patient data and one or more activity items generated from the patient data. The event elements and the predicted outcome elements are selectable to launch respective pop-up windows with additional information relating to the selected element.

18 Claims, 15 Drawing Sheets
(9 of 15 Drawing Sheet(s) Filed in Color)

(56)  References Cited

U.S. PATENT DOCUMENTS

| | | | |
|---|---|---|---|
| 11,289,187 B2 | 3/2022 | Mellem et al. | |
| 2017/0177795 A1 | 6/2017 | Mabotuwana et al. | |
| 2019/0392944 A1 | 12/2019 | Samset et al. | |
| 2020/0005911 A1* | 1/2020 | Brooks | G16H 15/00 |
| 2020/0234826 A1* | 7/2020 | Said | G16H 10/20 |
| 2021/0209757 A1 | 7/2021 | Min | |
| 2021/0264212 A1 | 8/2021 | Paik et al. | |
| 2021/0350937 A1* | 11/2021 | Lefkofsky | G16H 20/10 |
| 2022/0355123 A1 | 11/2022 | Engman et al. | |

OTHER PUBLICATIONS

International Application No. PCT/US2024/043674 filed on Aug. 23, 2024, International Search Report and Written Opinion issued Nov. 15, 2024, 11 pages.
Umlauft, D. et al., "Systems and Methods for Longitudinal Cardiology Timeline Presentation and Clinical Decision Support," U.S. Appl. No. 63/487,562, filed Feb. 28, 2023, 59 pages.

* cited by examiner

SYSTEMS AND METHODS FOR LONGITUDINAL TIMELINE PRESENTATION AND PREDICTIVE CLINICAL DECISION SUPPORT

FIELD

Embodiments of the subject matter disclosed herein relate to care guideline recommendations, and more particularly to an integrated cardiology timeline presentation system including clinical decision support.

BACKGROUND

Digital collection, processing, storage, and retrieval of patient medical records may include a conglomeration of large quantities of data. In some examples, the data may include numerous medical procedures and records generated during investigations of the patient, including a variety of examinations, such as blood tests, urine tests, pathology reports, image-based scans, etc. Duration of the diagnosis of a medical condition of a subject followed by treatment may be spread over time from a few days to a few months or even years in the case of chronic diseases, including cardiac or cardiology-related conditions, which may be diseases that take more than one year to cure/treat or in some instances may be lifelong. Over the course of diagnosing and treating chronic disease, the patient may undergo many different treatments and procedures and may move to different hospitals and/or geographic locations.

Physicians are increasingly relying on electronic medical record (EMR) systems to sort through historical health records of the patient during diagnosis, treatment, and monitoring of patient conditions. For patients with chronic cardiac conditions, hundreds or even thousands of EMRs entries may result from numerous visits. Information may also be included in various other data sources, such as radiology systems, picture archiving and communication systems, and many more. Sorting and extracting information from multiple data sources is slow and inefficient, increasing likelihood of missing records when determining care or treatment plans due to data being spread out across a large number of records.

BRIEF DESCRIPTION

In one example, a computing device comprises a display screen, the computing device configured to display on the display screen a menu listing one or more electronic medical records (EMRs) of one or more patients, and additionally being configured to display on the display screen a patient timeline graphical user interface (GUI) accessible from the menu, wherein the patient timeline GUI displays, for each patient, patient data as longitudinal medical history events and one or more predicted outcome elements of one or more corresponding parameters of a plurality of parameters of the patient data, the patient data obtained from the one or more EMRs and the one or more predicted outcome elements generated based at least in part on the patient data, wherein each element of the longitudinal medical history event elements and the one or more predicted outcome elements is selectable to launch a pop-up window with additional information related to the selected element, and wherein the patient timeline GUI is displayed while the one or more EMRs are in an unlaunched state.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood from reading the following description of non-limiting embodiments, with reference to the attached drawings, wherein below.

DETAILED DESCRIPTION

Figure 1:
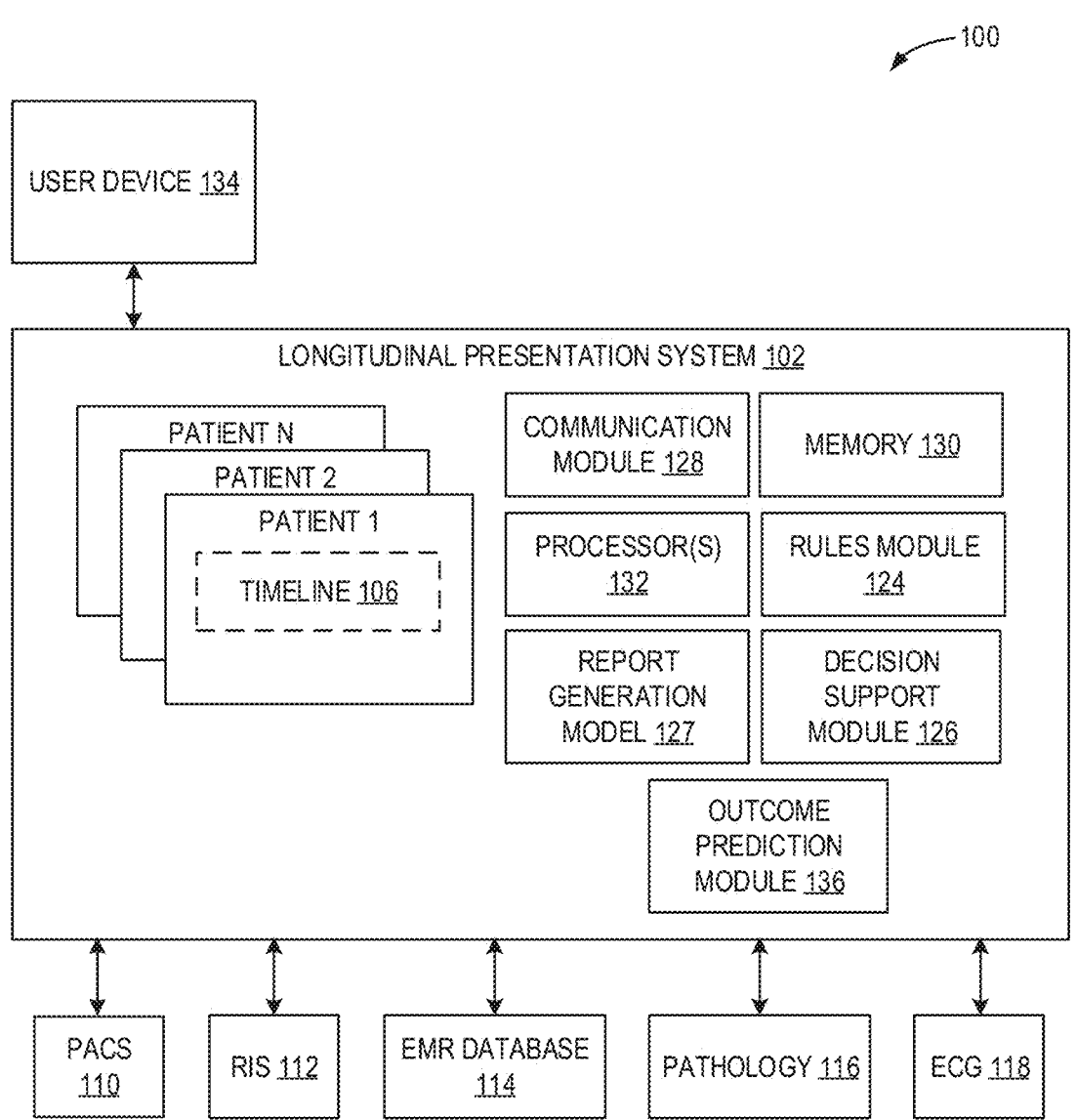
FIG. 1 shows a block diagram of an example system for displaying cardiology-focused clinical information of a patient to a user and generating clinical decision support.

The following description relates to various embodiments of a longitudinal patient history timeline and predictive clinical decision support system. In particular, systems and methods for a longitudinal patient history timeline and predictive clinical decision support system are provided for patient history analysis and display of longitudinal patient information that structures a patient's medical data into a visual longitudinal patient journey view as well as display of decision support that provides recommendation(s) for treatment and/or care and/or predicted outcomes of one or more of the recommendations to aid clinical thinking and guide actions to achieve efficiency and personalized patient experience.

Hospitals and other clinical facilities may provide computing systems with graphical user interfaces (GUIs) for displaying patient information to healthcare providers and other users. In this way, a healthcare provider may view historical and the most up-to-date patient information and retrieve data from electronic medical records (EMRs), imaging results, laboratory results, and so on. Further, alerts may be automatically and/or manually generated to indicate recommendations and/or guidelines for care of a patient. Such alerts are often retrieved from a single source (e.g., a single EMR system, a picture archiving and communication system (PACS), etc.). Retrieving information in this manner may result in display of only one data type or medical modality, and therefore falls short of comprehensive patient-centric analysis. For example, patient information retrieved from an EMR may exclude information of recently updated imaging. As such, care recommendations may not take into account results of the recently updated imaging and therefore are not comprehensive and recommendations for clinical decisions or treatment plans may be inaccurate and/or may not maximize patient outcomes.

Cardiovascular disease is an example of a common chronic condition that demands long term monitoring, treatment, and intervention, often over many years of a patient's life, therefore resulting in numerous encounters, exams, etc. Cardiovascular disease may include a variety of conditions including heart disease (coronary artery disease), heart attacks (myocardial infarctions), stroke (cerebrovascular accident), heart failure, arrhythmias, valvular disease, peripheral vascular disease, and more. Clinical and other medical data, such as imaging findings, laboratory results, vital signs, including blood pressure and heart rate, algorithmic scores, and heart rhythm findings, among others, are used to diagnose and monitor cardiovascular health of a patient. With long term monitoring and treatment of such a chronic disease, the medical data of a patient's past medical history may become vast and difficult to sort through when searching for specific information when making informed clinical decisions. As a result, cognitive overload and suboptimal care due to missing information may occur.

The methods and systems provided herein detail a longitudinal patient history timeline and predictive clinical decision support system. The patient history timeline may consolidate multiple types of medical data from a plurality of sources (e.g., a plurality of data repositories) into a single graphical user interface that enables users to easily review a patient's medical history, visualize and evaluate a health journey for a desired clinical setting (e.g., cardiology, oncology, etc.), review response to various treatments and/interventions, and formulate future decisions about a patient's care. The system further analyzes the medical data to generate one or more activity recommendations based on known care guidelines. One or more of the activities may be selectable to generate predicted outcomes via one or more determined algorithms. The user may accept, reject, or propose alternative activities within a clinical decision support interface and may export a resulting care plan for their own use as well as for patient use.

Via user interactions with graphical user interfaces, the user (e.g., the care provider) may view patient data in various forms, including in brief small text as well as in detailed views via user selection of elements (e.g., hovering over an element to launch a pop-up window). Further, user interaction may designate which of the recommended activities are to be included in a care plan for the patient. The recommended activities and predicted outcomes for one or more parameters based on one or more of the recommended activities may guide the care provider in decision making, thereby reducing cognitive overload and providing increased efficiency.

Embodiments of the present disclosure will now be described, by way of example, with reference to the figures, in which FIG. 1 schematically shows an example patient information system 100 that may be implemented in medical facility such as a hospital. Patient information system 100 may be a portion of or otherwise included in a computing device and/or computing system. Patient information system 100 may include a longitudinal presentation system 102. Presentation system 102 may include resources (e.g., memory 130, processor(s) 132) that may be allocated to store and execute timelines for each of a plurality of patients. For example, as shown in FIG. 1, timeline 106 is stored on presentation system 102 for a first patient (patient 1); a plurality of additional timelines may be stored on and/or generated by presentation system 102, each corresponding to a respective patient (patient 2 up to patient N).

Each timeline 106 may include graphical representations of patient medical events arranged chronologically, as will be described with reference to FIG. 7. The patient medical events depicted on the timeline 106 may include office or hospital visits (and information gathered during such visits), findings from diagnostic imaging, pathology reports, lab test results, algorithmic scores, and any other clinically relevant information. Further, the patient medical information, including medical history, current state, vital signs, and other information, may be analyzed by a decision support module 126, which may be used to generate and output recommendations for care and/or treatment.

The patient information that is presented via the timeline 106 may be stored in different medical databases or storage systems (e.g., data repositories) in communication with presentation system 102. For example, as shown, the presentation system 102 may be in communication with a PACS 110, a radiology information system (RIS) 112, an EMR database 114, a pathology database 116, and an electrocardiogram (ECG) management system 118, and/or other data sources such as a clinical information system (CIS), hospital information system (HIS), or others. PACS 110 may store medical images and associated reports (e.g., clinician findings), such as ultrasound images, MRI images, etc. PACS 110 may store images and communicate according to digital imaging and communications in medicine (DICOM) format. RIS 112 may store radiology images and associated reports, such as computerized tomography (CT) images, X-ray images, etc. EMR database 114 store electronic medical records for a plurality of patients. EMR database 114 may be a database stored in a mass storage device configured to communicate with secure channels (e.g., HTTPS and TLS), and store data in encrypted form. Further, the EMR database is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc. Pathology database 116 may store pathology images and related reports, which may include visible light or fluorescence images of tissue, such as immunohistochemistry (IHC) images. ECG management system 118 may store data of ECG tracings, including results of ECGs (e.g., heart rate, rhythm, parameters like QT interval and QRS complex).

When requested, timeline 106 may be displayed on the one or more display devices. As shown in FIG. 1, a user device 134, and in some examples more than one user device, may be communicatively coupled to presentation system 102. Each user device may include a processor, memory, communication module, user input device, display (e.g., screen or monitor), and/or other subsystems and may be in the form of a desktop computing device, a laptop computing device, a tablet, a smart phone, or other device. Some user devices, such as care provider devices, may be adapted to send and receive encrypted data and display medical information, including medical images in a suitable format such as DICOM or other standards. In some examples, one or more of the user devices may be located locally at the medical facility (such as in a room of a patient or a clinician's office) and/or remotely from the medical facility (such as a care provider's mobile device). In other examples, the user device may be a personal device of a patient configured to access the presentation system 102 remotely.

In some examples, the timeline 106 may be configured based on the user that is viewing it. For example, the timeline 106 may be configured as a patient-oriented timeline GUI when the user is a patient, as is determined based on type of account, type of user device, or other means. In another example, the timeline 106 may be configured as a clinician-oriented timeline GUI when the user is a care provider, as is determined based on type of account, type of user device, or other means. As will be described with respect to FIG. 3, the patient-oriented timeline GUI may display a first subset of the obtained patient data based on one or more rule sets and the clinician oriented timeline GUI may display a second subset of the obtained patient data based on one or more rule sets.

When viewing timeline 106 via a display of a user device, a care provider or other user such as a patient may enter input (e.g., via the user input device, which may include a keyboard, mouse, microphone, touch screen, stylus, or other device) that may be processed by the care provider device and sent to the presentation system 102. In examples where the user input is a selection of a link or user interface control button/element of the timeline, the user input may trigger display of a selected EMR, trigger progression to a desired point in time or view of the timeline (e.g., trigger display of desired patient medical information), trigger display of various conditions in the timeline or display of information specific to a condition or event, trigger updates to the configuration of the timeline, trigger modification of the patient timeline GUI with display of a clinical decision support GUI, or other actions.

In some examples, the presentation system 102 may include the decision support module 126 that may be configured to analyze patient data obtained from the plurality of sources (e.g., EMR database 114, PACS 110, RIS 112, pathology database 116, and/or ECG management system 118). The patient data may include patient history events and information relevant to those events, including dates of evaluation and findings for imaging data, laboratory results, vital signs, pathology, ECG data, hospitalization records, and more. The decision support module 126 may be in communication with a rules module 124. The rules module 124 may include rule sets and criteria for a plurality of guideline recommendations. In some examples, guideline recommendations may be sourced from a widely available (e.g., publically published) source (e.g., guidelines from American College of Cardiology (ACC) and/or European Society of Cardiology (ESC)) and may be storied in memory 130 of the patient information system 100. In other examples, guideline recommendations may be customizable for configuration by a user (e.g., a clinical expert or authorized care provider).

Criteria for a guideline recommendation may include one or more triggers (e.g., patient data acquired from the plurality of sources) that may be met in order for the guideline recommendation to be indicated. Each trigger may be defined based on a procedure code stored in the memory 130 and thus determination of whether a particular trigger has been met may be based on a procedure code within patient information (e.g., an EMR) matching a procedure code stored in memory as part of the criteria for guideline recommendations. A procedure code may define what was done or administered to a patient in a clinical setting, this may be a surgical procedure, a screening test, a diagnostic exam, a medication, a diagnosis given to the patient, an algorithmic score defined for the patient, among others. Codes are alphanumeric and allow for identification of terminology in data repositories to identify triggers. Types of terminologies include International Classification of Diseases (ICD)-10 codes, Current Procedural Terminology (CPT) codes, RxNorm, and the like. In some examples, the procedure code that defines (e.g., identifies) triggers, which is stored in the memory 130, may be determined automatically by the patient information system 100. In other examples, the procedure code that defines triggers may be configured manually by a clinical expert or care provider and inputted into the system for storage in memory 130. Further, in some examples, a user may configure from which source guideline recommendations are taken, for example either the ACC or the ESC, if a care region is specified or user preference is had.

Each guideline recommendation may include or otherwise prescribe one or more activities. Activities may be treatments, interventions, or other types of care that may be prescribed to a patient. When recommended based on an indicated guideline recommendation, an activity may be displayed as an activity item (e.g., an activity recommendation) to the user via a clinical decision support interface. Rule sets may include trigger combinations that may be met in order for an activity of an indicated guideline recommendation to be suggested for a specified patient. Each rule set may include a decision tree that includes parameter connectors "AND", "OR", and/or "AND/OR" that define relationships between parameters. Combinations with AND must include each parameter connected with the AND. Combinations with OR may include any of the parameters connected with the OR. Combinations with AND/OR may include one or both (or all, for combinations including more than two parameters) parameters connected with the AND/OR. Trigger combination strings may include multiple connections, wherein each parameter is connected to at least one other parameter via a parameter connector.

As a non-limiting example, for an activity suggesting opportunistic screening for atrial fibrillation, a first parameter may be no historical diagnosis of atrial fibrillation, a second parameter may be arterial hypertension, and a third parameter may be no ECG within 180 days. A decision tree of a rule set corresponding to the activity may stipulate that the first parameter AND the second parameter AND the third parameter must be met in order for the activity to be identified. Patient data that includes no history of atrial fibrillation, a current diagnosis of hypertension, and a most recent ECG dated 2 years previous may satisfy the rule set and the corresponding activity may be displayed as an activity item for the patient. Conversely, patient data that includes no history of atrial fibrillation and a current diagnosis of hypertension, but a most recent ECG is dated 15 days previous may not satisfy the rule set as the third parameter is not met and therefore the corresponding activity may not be displayed as an activity item for the patient. Satisfaction of the rule set may be determined based on the decision tree therein, whereby a decision tree algorithm and matching of procedure codes determines whether parameters/triggers are met by patient data. In this way, only relevant recommendations are displayed for a patient of interest.

Determination of activities may be performed by a decision tree algorithm of the decision support module 126 based on the defined rule sets or based on another suitable mechanism. Each decision tree and rule set may be stored in memory 130 and accessed to perform an associated decision tree algorithm. Decision trees and the decision tree algorithms used to determine activities may also be configurable, in some examples. As an example, the system may allow a user to add, modify, or delete one or more decision trees or algorithms used to generate activity recommendations.

The rules module 124 may further include period segmentation rules. The period segmentation rules may arrange the patient data chronologically and group (e.g., segment) patient data into a plurality of events. For example, medical data obtained from the plurality of sources for a specified patient may include data of a plurality of events such as hospitalizations, encounters, exams (e.g., imaging exams or other), disease events (e.g., strokes, heart attacks, heart failure exacerbations, new arrhythmias, among others), medication changes (e.g., starts, stops, or dosage changes), and more. Each of the plurality of events may include one or more data points at various points in time. The period segmentation rules may group the patient data into the plurality of events and arrange each data point for each event chronologically. In this way, different events may be displayed on separate time aligned panels and/or graphs of a plurality of panels and graphs in a way that organizes the patient data to be easily visualized by the care provider, thereby increasing efficiency and decreasing cognitive overload.

In some examples, the presentation system 102 may include a report generation model 127 that may be configured to generate patient-customized report templates based on accepted activity items from within the clinical decision support GUI. The report generation model 127 may include one or more rule sets for each activity to generate information relevant to each activity accepted for a specified patient. For example, in an example in which an activity item is a medication change, the report generation model 127 may generate information related to prior prescription, new prescription (including information of dosage, frequency, number of pills prescribed, etc.), instructions for use, and more, which may be included in a generated report of a care plan.

A management application executed of the presentation system 102 may allow an administrator to configure how the timelines are displayed, what information is conveyed by the timelines for each patient, etc. The management application may include an interface for configuring hospital specific protocols and guidelines for generating and displaying the timelines. The management application may further allow the administrator, clinical expert, or authorized care provider to modify criteria and/or rule sets for guideline recommendations and/or activities. In some examples, modifications made to criteria and/or rule sets may be personalized to a specific care provider. In other examples, modifications to criteria and/or rule sets may be made for a medical facility, network, or other entity in which changes made apply to each user within the entity. The management application may further allow a user to indicate whether a patient-oriented timeline GUI or a clinician-oriented timeline GUI is to be displayed. As will be described further with respect to FIG. 3, user selection, determination of type of user device, etc. may indicate to the system whether the patient-oriented timeline GUI or the clinician-oriented timeline GUI is selected. The patient-oriented timeline GUI may display a first subset of patient data and/or activity recommendations and the clinician-oriented timeline GUI may display a second subset of patient data and/or activity recommendations. For example, the patient-oriented timeline GUI may include lifestyle activity recommendations and/or activity recommendations selected by a clinician for the patient while the clinician-oriented timeline GUI may display all determined activity recommendations as well as information detail how/why each activity was determined.

Presentation system 102 may further include an outcome prediction module 136. As will be further described with respect to FIG. 2, the outcome prediction module 136 may include and/or otherwise communicate with one or more algorithms to generate outcome predictions for one or more parameters based on the processed patient data and activity recommendations. The one or more parameters may be lab results, vital signs, conditions, etc. that may be included in the patient data. The patient data may include a trend of values/conditions for each parameter and based on those values/conditions for the parameter, the outcome prediction module 136 may generate an outcome prediction for the parameter based on one or more selected activity recommendations.

Presentation system 102 may further include a communication module 128, memory 130, and processor(s) 132 to store and generate the timelines, as well as send and receive communications, GUIs, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., DICOM, Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 may include one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multiprocessor system, and, thus, may include one or more additional processors that are identical or similar to each other and that are communicatively coupled via an inter-connection bus. As an example, the decision support module 126 may store instructions for generating activity items in the memory 130 that are executable by the processor(s) 132.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally, or alternatively, one or more of these devices may be hard-wired with logic circuits to perform these operations.

Thus, presentation system 102 may be configured to obtain/ingest medical data from a variety of sources (e.g., PACS, EMR, RIS, etc.) and analyze, extract, and register selected medical data to generate a timeline and activity item(s) for each patient as described herein. In some examples, presentation system 102 may include one or more data filters (e.g., AI-assisted data filters) configured to monitor and filter the ingested data to ensure that only relevant and complete data is presented in the timeline. In some examples, an indication of the level of confidence in the data may be presented with an icon in each timeline. This adds to the confidence factors in a clinical solution and guideline recommendations and also leans towards being representative of precision health. This would apply to quality checks on imaging data and IQ evaluation of digital pathology, radiology (ensuring appropriateness of protocols for the condition adjudged).

One or more of the devices described herein may be implemented over a cloud or other computer network. For example, presentation system 102 is shown in FIG. 1 as constituting a single entity, but it is to be understood that presentation system 102 may be distributed across multiple devices, such as across multiple servers. Further, while the elements of FIG. 1 are shown as being housed at a single medical facility, it is to be appreciated that any of the components described herein (e.g., EMR database, RIS, PACS, etc.) may be located off-site or remote from the presentation system 102. Further, the longitudinal data utilized by the presentation system 102 for the timeline generation and other tasks described below could come from systems within the medical facility or obtained through electronic means (e.g., over a network) from other referring institutions.

While not specifically shown in FIG. 1, additional devices described herein (e.g., user device 134) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., user device 134) may store user interface templates in memory that include placeholders for relevant information stored on presentation system 102 or sent via presentation system 102. For example, user device 134 may store a user interface template for a patient timeline that a user of user device 134 may configure with placeholders for desired patient information. When the timeline is displayed on the care provider device, the relevant patient information may be retrieved from presentation system 102 and inserted in the placeholders. The user input devices may include keyboards, mice, touch screens, microphones, or other suitable devices.

Figure 2:
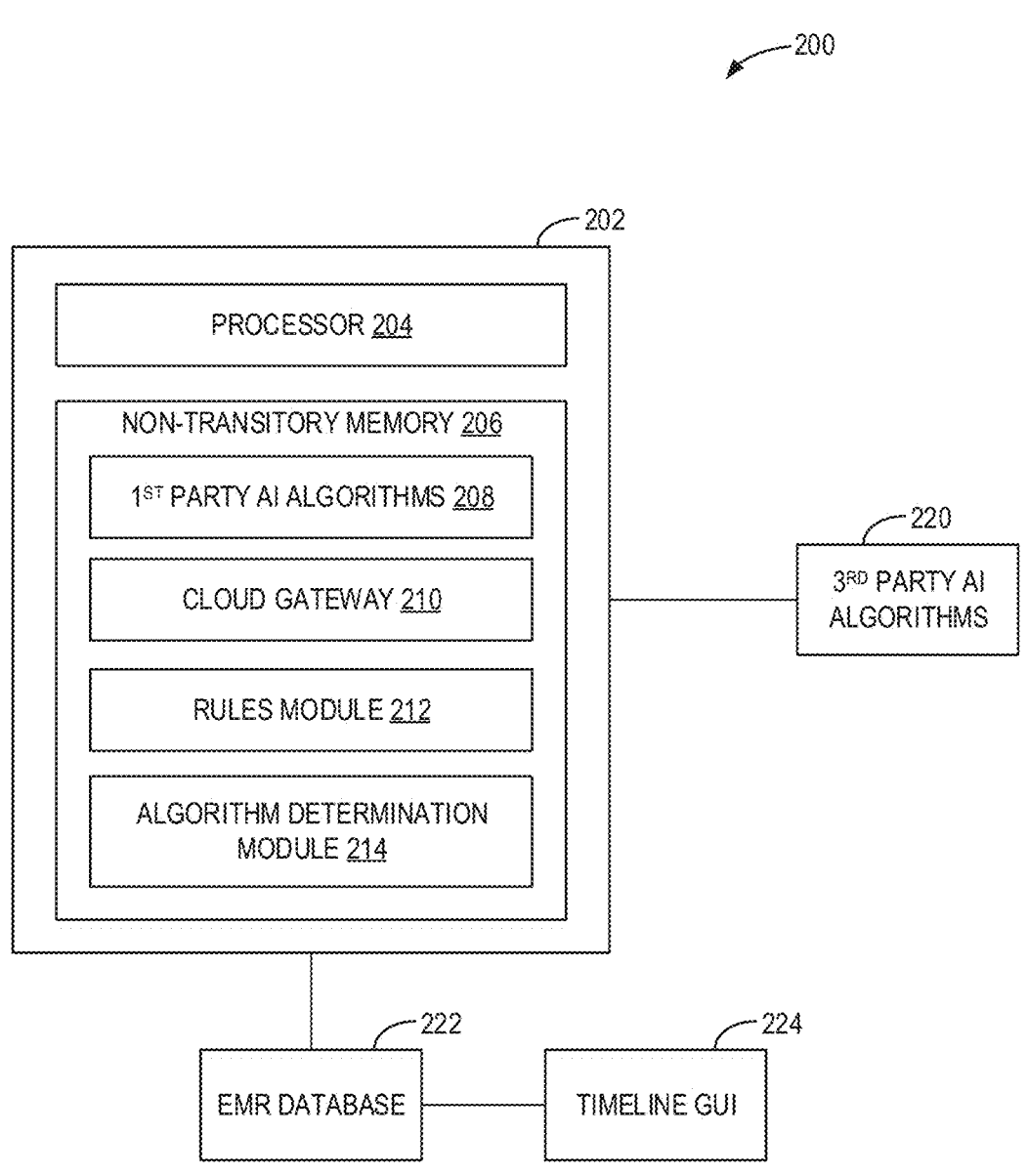
FIG. 2 shows a block diagram of an example data processing system.

Referring to FIG. 2, a data processing system 200 is shown, in accordance with an exemplary embodiment. In some examples, data processing system 200 may be incorporated into the patient information system 100 of FIG. 1. For example, the data processing system 200 may be provided in the patient information system 100 within or otherwise disposed with the longitudinal presentation system 102. In some examples, at least a portion of the data processing system 200 is disposed at a device (e.g., edge device, server, etc.) communicably coupled to the patient information system 100. Data processing system 200 may include an outcome prediction module 202, an EMR database 222, and a timeline GUI 224. The outcome prediction module 202 may be the outcome prediction module 136 of the longitudinal presentation system 102 of FIG. 1. The outcome prediction module 202 may be communicably coupled to the EMR database 222 to gather data of a patient's medical history. The EMR database 222, as is described with respect to FIG. 1, may be communicably coupled to the timeline GUI 224 wherein patient history data from the EMR database is acquired, processed, longitudinally segmented and presented in timelines for display on a user device, such as a care provider device, within the timeline GUI 224.

The outcome prediction module 202 may comprise a processor 204 configured to execute machine readable instructions stored in non-transitory memory 206. Processor 204 may be single core or multi-core, and the programs executed thereon may be configured for parallel or distributed processing. In some examples, the processor 204 may optionally include individual components that are distributed throughout two or more devices, which may be remotely located and/or configured for coordinated processing. In some examples, one or more aspects of the processor 204 may be virtualized and executed by remotely-accessible networked computing devices configured in a cloud computing configuration. In some examples, the outcome prediction module 202 may be or may be at least a part of an orchestrator system that obtains and processes data and then via connections to a display device/GUI, displays the processed data in the GUI.

Non-transitory memory 206 may store first party artificial intelligence (AI) algorithms 208, a cloud gateway 210, a rules module 212, and an algorithm determination module 214. The first party AI algorithms 208 may include one or more algorithms to determine predicted outcomes of one or more parameters based on specific selected activities and respective patient data. For example a first algorithm may determine a predicted outcome for a patient's blood pressure based on selection of an activity including adding an anti-hypertensive while a second algorithm may determine a predicted outcome for a patient's renal function based on selection of an activity including adding a diuretic. In some examples, both the first and second algorithms may be executed based on selection of an activity recommendation. For example, starting a medication that may change both blood pressure and renal function, such as a thiazide diuretic, may indicate execution of both the first and second algorithm.

The cloud gateway 210 may allow the processor 204 to connect to a cloud computing platform, in some examples allowing the outcome prediction module 202 to be communicably coupled to third party AI algorithms 220. The third party AI algorithms 220 may be stored external to the non-transitory memory 206 but may be accessible by the outcome prediction module 202 via the cloud gateway 210. Various combinations of algorithms may be possible, including combinations including both first and third party algorithms, based on one or more selected activities, available or plotted parameters, and the patient data.

Which algorithm(s) are executed to generate an outcome prediction for one or more parameters, including both first party and third party algorithms, may be determined based on the rules module 212 and the algorithm determination module 214. Based on sets of rules 212 stored in the rules module 212, the algorithm determination module 214 may determine which algorithms the processor 204 executes. For example, based on one or more selected activities and processed patient data for a given patient, the algorithm determination module 214 may determine which first party and/or which third party algorithms to use to generate the outcome prediction based on rules in the rules module 212. In some examples, the predicted outcomes may comprise a projected trend, a predicted data point, or a combination thereof.

In this way, the data processing system 200 may use the patient data obtained by the patient information system 100, generated activity recommendations, and user inputs selecting one or more of the activity recommendations in order to determine and display outcome predictions for one or more parameters of the patient data. The data processing system 200, via cloud computing platforms and gateways, may use both external algorithms stored separate from the outcome prediction module and internal algorithms stored within the outcome prediction module.

Figure 3:
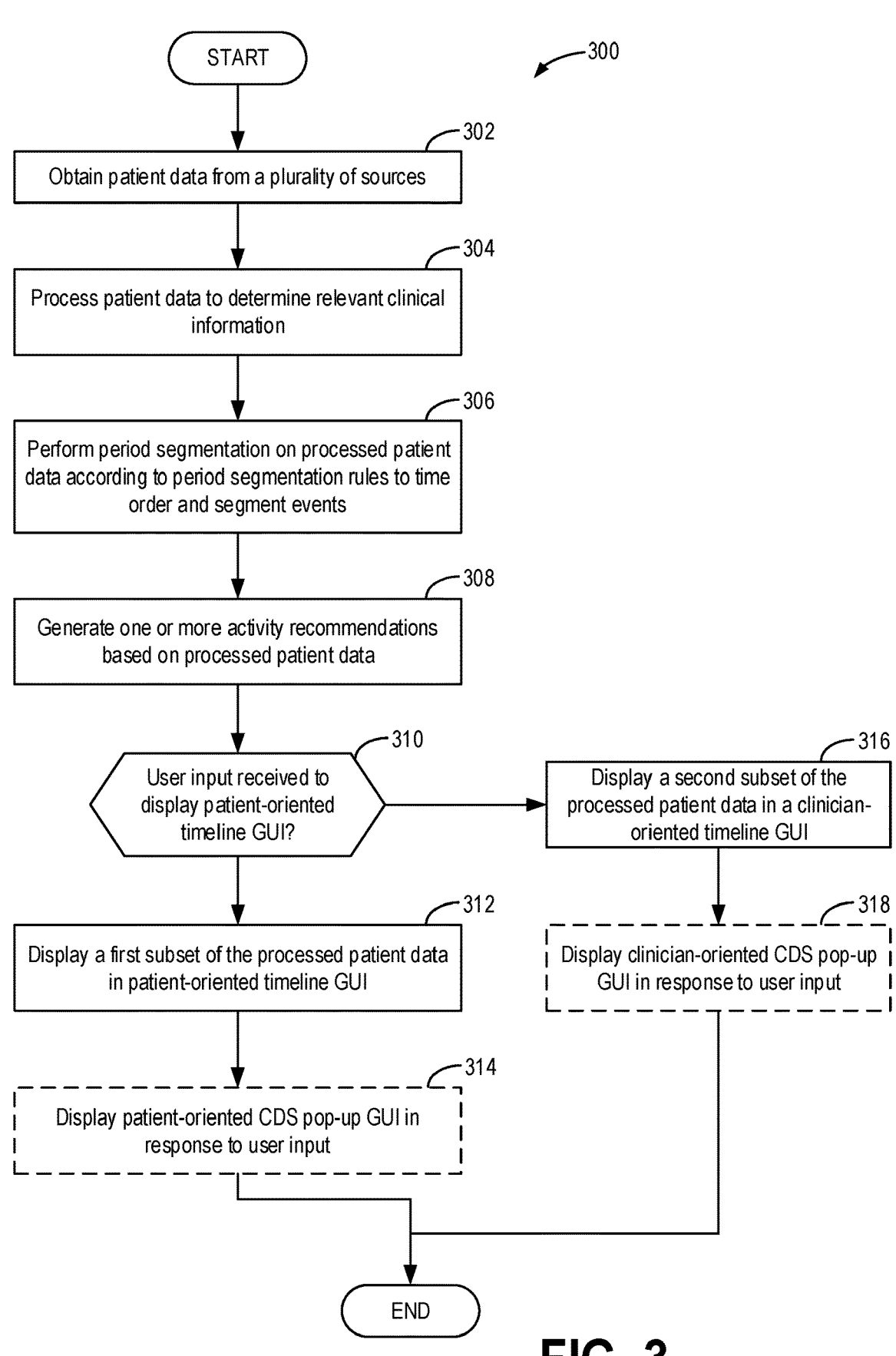
FIG. 3 is a flowchart illustrating a method for generating and displaying a timeline graphical user interface (GUI) and one or more activity items for a patient.

Turning now to FIG. 3, a flowchart illustrating a method 300 for generating a timeline and one or more activities for a patient is shown. Method 300 may be carried out according to instructions stored in memory of a computing device (e.g., memory 130 of presentation system 102 of FIG. 1), which may be executed by a processor of the computing device (e.g., processor(s) 132). While method 300 is described specific to one patient, at least portions of method 300 may be performed simultaneously for a plurality of patients. The method 300 will be described with respect to the systems of FIGS. 1-2, though it should be understood that similar methods may be performed via other systems.

At 302, patient data from a plurality of sources is obtained for the patient. The patient data may be obtained from EMR databases, PACS, HIS/RIS/CIS, pathology systems, and more, as described previously with respect to FIG. 1. The patient data may include information of prior hospitalizations, pathology results, imaging exam findings, laboratory values, vital signs, medications, diagnosed conditions, and more. The patient data may include dates corresponding to each datum. The patient data may include all available data from each of the plurality of sources specific to the patient. The patient data may be obtained in response to a request (e.g., a user input or selection) to display a timeline of a patient information/past medical history or automatically in response to an application being launched. For example, when viewing an EMR for the patient, a user may select a link displayed as part of the EMR interface in order to initiate generation of the timeline for the patient.

At 304, the patient data is processed to determine relevant clinical information. A desired clinical setting may be introduced/defined to determine relevancy. In some examples, the desired clinical settings may be defined by user selection of a clinical setting from a list of possible clinical settings launching the presentation system. For example, a link within an EMR that launches the patient timeline may be include a drop=down menu through which the user may select a desired clinical setting. As another example, the patient timeline system, as a standalone application, may include an initial start page with a drop-down menu through which the user may select a desired clinical setting. In other examples, the desired clinical setting may be defined automatically based on an EMR from which the patient timeline was launched. For example, launching the patient timeline from an ECG management system may automatically define the desired clinical setting as cardiology.

In some examples, as will be shown in FIGS. 7-15, the timeline and the one or more activities ultimately generated/recommended may be aimed at a desired clinical setting and, as such, data of the patient determined to be irrelevant to the desired clinical setting may be processed or filtered out of the patient data. In this way, irrelevant information may be omitted from the timeline and activities recommended may be tuned to the desired clinical setting. In some examples, determination of relevancy may be based on one or more rules of a rules module of the patient information system (e.g., rules module 124 of FIG. 1), wherein types of data are predefined as relevant or irrelevant to various clinical settings.

At 306, period segmentation is performed on the processed patient data according to period segmentation rules to time order and segment events. The period segmentation rules may be included in the rules module of the patient information system. The patient data processed at 304 may include multiple parameters of data of the patient's history, including clinical data, ECG data, and/or others, as well as multiple types of data within each parameter. As will be described further below, data may be partitioned into various categories, parameters, and the like so as to define diagnoses, conditions, encounters of certain types. For examples, data relevant to a condition such as atrial fibrillation may be segmented from data relevant to an imaging finding such as ejection fraction (indicating presence and severity of congestive heart failure). As a result, data may be presented in groups, wherein, for example, a time aligned graph display information of a selected group and excludes data not included in the selected group. As described, each of the data may include a corresponding date (e.g., a date of diagnosis, a date of hospitalization, a date of procedure, etc.). Period segmentation may time order the patient data chronologically such that presentation of the data (e.g., display of the data within a patient timeline GUI) may be arranged chronologically.

At 308, one or more activity recommendations are generated based on the processed patient data. The processed patient data may be analyzed by a decision support module (e.g., decision support module 126 of FIG. 1) to determine which guideline recommendations have been met by the processed patient data (e.g., satisfying one or more rule sets). In some examples, indicated guideline recommendations based on the processed patient data may trigger generation of one or more activity recommendations. As will be further described with respect to FIG. 6, activity recommendations may be determined based on identification of criteria for particular guidelines and application of rule sets to patient data that meets the identified criteria.

At 310, the method 300 determines whether user input is received to display a patient-oriented timeline GUI. As is described with respect to FIG. 1, displayed timeline GUIs may either be patient-oriented or clinician oriented. User input may include selection of an element corresponding to one of the timeline GUIs, input of user specifics (e.g., logging in to a particular system with a username linked to a particular account type), and the like. If user input indicates that the patient-oriented timeline GUI is to be displayed (YES at 310), method 300 proceeds to 312. If user input indicates that the clinician-oriented timeline GUI is to be displayed (NO at 310), method 300 proceeds to 316.

At 312, a first subset of the processed patient data is displayed within the patient-oriented timeline GUI. The patient-oriented timeline GUI may be displayed on a display of a user device (e.g., desktop computer, a laptop computer, a smart phone, tablet, etc.). The patient-oriented timeline GUI may include various panels presenting the first subset of the processed patient data in a chronological manner. The first subset of the processed patient data may include data relevant to a layperson, such as vital signs, lab values, current/past medications, hospitalization dates, diagnosed conditions, and the like. The first subset of the processed patient data may not include data not relevant to the layperson, such as sources of information descriptions (e.g., sources of a range for a particular lab value).

Displaying the first subset in a chronological manner may include displaying a plurality of time aligned graphs/panels/ etc. For example, a time aligned graph may be displayed indicating events for a chosen condition or other type of parameter and an event history panel may be displayed including time aligned event icons for a plurality of event types such as hospitalizations, procedures, and encounters. Each of the event icons or points on the time aligned graph may be selectable to display a limited list of additional information.

Optionally at 314, a patient-oriented clinical decision support GUI is displayed in response to user input. The patient-oriented clinical decision support GUI may display a subset of the one or more activity recommendations for review by the patient. In some examples, the first subset of the one or more activity recommendations may include lifestyle-oriented activity recommendations, as designated by the rules module. For example, the first subset may include activity recommendations such as "quit smoking" and/or "reduce alcohol intake" but may not include activity recommendations that demand interaction from a clinician, such as starting a new medication. In some examples, the first subset may include activity recommendations that have been accepted by the patient's corresponding clinician. In this way, the accepted recommendations may be selectable so to show the patient viewing the patient-oriented timeline GUI which recommendations their clinician/physician agrees with.

At 316, a second subset of the processed patient data is displayed within the clinician-oriented timeline GUI. The clinician-oriented timeline GUI may be displayed on a display of a care provider device (e.g., user device 134 of FIG. 1). The clinician-oriented timeline GUI may include various panels presenting the second subset of the processed patient data in a chronological manner. The second subset of the processed patient data may include data relevant to the clinician, such as vital signs, lab values, current/past medications, hospitalization dates, diagnosed conditions, and the like, including data such as sources of information descriptions (e.g., sources of a range for a particular lab value).

Similar to the first subset, displaying the second subset in a chronological manner may include displaying one or more time aligned graphs/panels/etc. For example, a time aligned graph may be displayed indicating events for a chosen condition or other type of data and an event history panel may be displayed including time aligned event icons for a plurality of event types such as hospitalizations, procedures, and encounters. Each of the event icons or points on the time aligned graph may be selectable to display a limited list of additional information.

Optionally at 318, a clinician-oriented clinical decision support GUI is displayed in response to user input. The clinician-oriented clinical decision support GUI may display the one or more activity recommendations for review by the clinician. In some examples, the one or more activity recommendations may include lifestyle-oriented activity recommendations, as designated by the rules module, similar to the first subset of the one or more activity recommendations displayed in the patient-oriented clinical decision support GUI discussed above, as well as activity recommendations including adding/stopping/changing medications, proceeding with a procedure, proceeding with a screening, etc. In some examples, the one or more activity recommendations may include all recommended activities that have yet to be accepted as well as information specific to particular activities, including reasoning for why the activity is recommended, including references to sources such as ACS and/or ESC. Further, the activity recommendations may be selectable so to display to the user viewing the clinician-oriented timeline GUI which recommendations have been suggested based on the patient data.

Each of the activity recommendations may be displayed within the clinician-oriented clinical decision support GUI as an activity item that may be accepted or rejected via user inputs. The clinician-oriented clinical decision support GUI may include a plurality of tabs, including a first tab displaying pending activity items that have yet to be accepted or rejected, a second tab displaying accepted activity items and information specific to each accepted activity item, and a third tab displaying past activities that have been completed.

Figure 4:
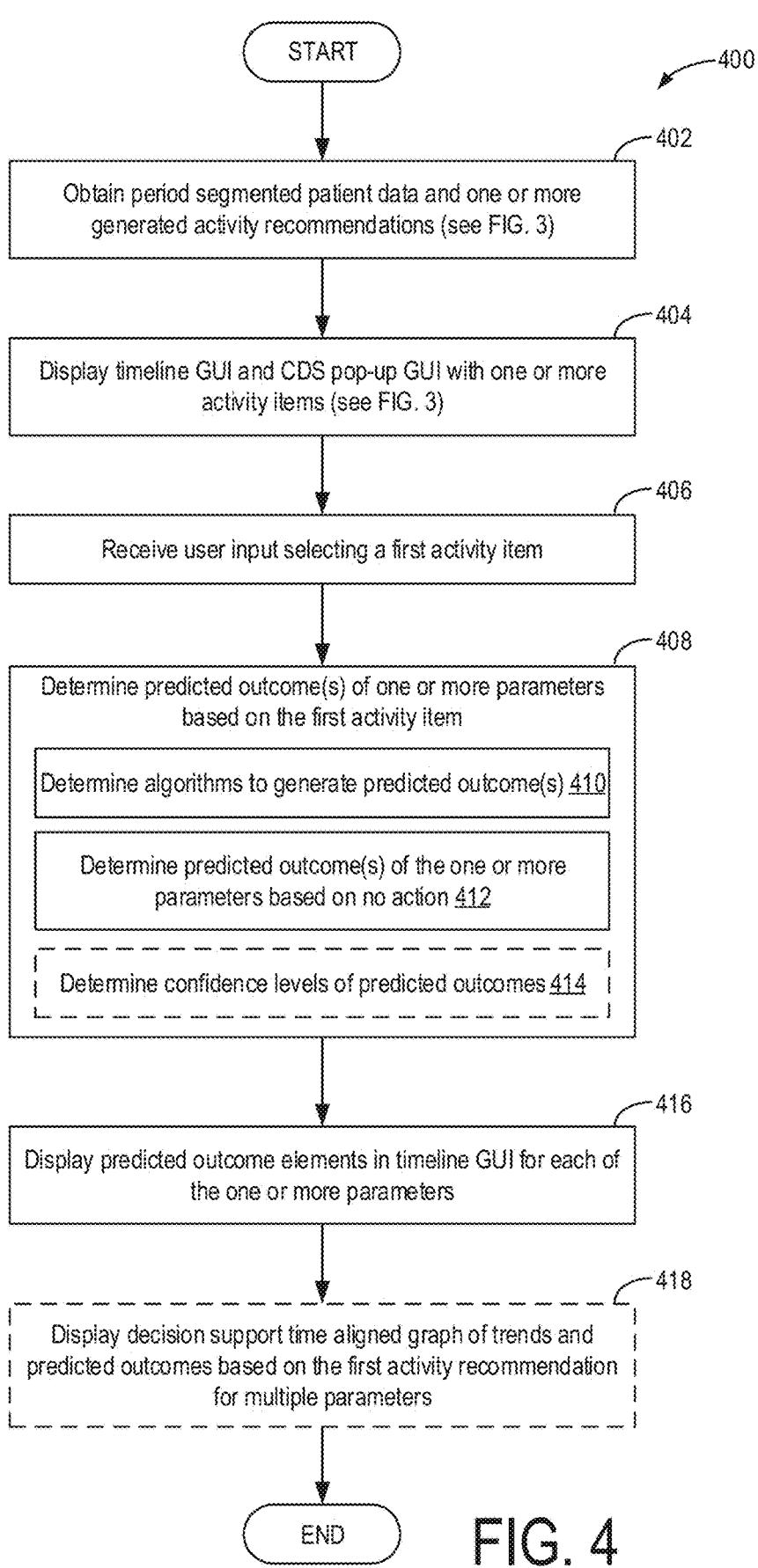
FIG. 4 is a flowchart illustrating a method for generating and displaying a predicted outcome of one or more parameters based on a selected activity item.

Referring now to FIG. 4, a flowchart illustrating a method 400 for determining predictive outcomes of one or more parameters based on a selected activity recommendation is shown. Method 400 may be carried out according to instructions stored in memory of a computing device (e.g., memory 130 of presentation system 102 of FIG. 1), which may be executed by a processor of the computing device (e.g., processor(s) 132). While method 400 is described specific to one patient, at least portions of method 400 may be performed simultaneously for a plurality of patients. The method 400 will be described with respect to the systems of FIGS. 1-2, though it should be understood that similar methods may be performed via other systems.

At 402, period segmented data and one or more generated activity recommendations are obtained. As is described above with respect to FIG. 3, patient data may be obtained from one or more databases, including one or more EMRs, PACS, and the like. The patient data may then be processed to exclude data not relevant to a desired clinical setting. The processed patient data may be period segmented to time align data events in groups in a chronological manner. Based on the processed patient data, one or more activity recommendations may be determined, as will be further described with respect to FIG. 6.

At 404, a timeline GUI and a clinical decision support GUI (e.g., a pop-up panel) with one or more activity items is displayed. Also as described with respect to FIG. 3, based on the period segmented processed patient data, the patient timeline GUI may be generated. The patient timeline GUI may display time aligned graphs, history event panels, and more showing the processed patient data in a chronological manner. The patient timeline GUI may include one or more types of selectable elements that when hovered over and/or selected, launch various windows or perform actions. One of the selectable elements may launch the clinical decision support GUI as a side panel when selected. The clinical decision support GUI may display the one or more activity recommendations as activity items in a list. Pending activity items (e.g., activity items not yet accepted or rejected) may be displayed in a pending tab, accepted activity items may be displayed in a care plan tab, and completed activities may be displayed in a past activity tab.

At 406, user input selecting a first activity item is received. The first activity item may be selected from the clinical decision support GUI. In some examples the first activity item may be selected from the pending tab and in other examples the first activity item may be selected from the care plan tab.

At 408, predictive outcome(s) of one or more parameters is determined based on the first activity item. Determining the predictive outcome(s) of the one or more parameters may include applying one or more AI algorithms to the processed patient data to determine the predicted outcome(s). As is described with respect to FIG. 2, an algorithm determination module and a rules module may determine the algorithms to use to generate the predicted outcome(s) based on the processed patient data and the selected activity item, as noted at 410. In some examples, the algorithm determination module and the rules module may determine more than one algorithm to be used.

In addition to determining predicted outcome(s) of the one or more parameters based on the first activity item, predicted outcomes may also be determined for the one or more parameters based on a "no action" condition, as noted at 412. In some examples, a no action condition outcome prediction element may be selected (e.g., toggled to on) to generate the no action predicted outcome(s). The no action condition may indicate that no activity item is selected and algorithm(s) may determine a predicted outcome for each parameter in the condition that no changes are made to the patient's care. In some examples, one or more of the algorithms determined to generate the predicted outcome(s) for the first activity item may differ from one or more of the algorithms determined to generate the predicted outcome(s) for the no action condition.

In some examples, confidence levels of the determined predicted outcome(s) may be determined as well, as noted at 414. The confidence levels may be determined based on corresponding algorithm(s) used to determine the predicted outcome(s). In some examples, confidence levels may be determined for both the first activity item as well as the no action condition. Confidence levels may be determined as percentages, decimals, or other value. In some examples, predicted outcomes may be generated for a specified amount of time, for example the predicted data points may be determined for 1 day, 1 week, 6 weeks, 6 months or other suitable time frame from a current date. In other examples, predicted outcomes may be generated for specific time periods, wherein a predicted outcome is determined for a first time and for a second time, wherein the predicted outcome of the parameter for the first time may differ from the second time. For example, for an activity item of starting an antihypertensive medication, a predicted outcome of a blood pressure parameter at a first time of 1 week after a start date may be a first value and a predicted outcome of the blood pressure parameter at a second time of 1 month after the start date may be a second value, wherein the second value demonstrates that the patient's blood pressure may be lower at the second time than the first time based on the algorithm.

At 416, predicted outcome elements representing the predicted outcomes are displayed in the patient timeline GUI for each of the one or more parameters. In some examples, the representations of the predicted outcomes may be displayed in response to user selection of a decision support element within the GUI. As described above, the patient timeline GUI may include time aligned graphs, event panels, etc., through which time aligned data of one or more parameters may be displayed. For example, a time aligned graph of an atrial fibrillation burden parameter may be included in the patient timeline GUI. A time aligned plot of the time aligned graph of atrial fibrillation burden may include a plurality of data points based on the processed patient data, wherein data points belong to a date as an x coordinate and a parameter sub-type as a y-coordinate, wherein the parameter sub-types, for the example parameter of atrial fibrillation burden, are no atrial fibrillation, paroxysmal, persistent, and permanent. The time aligned plot may include for future dates a future portion including the predicted outcome element(s) for the atrial fibrillation burden parameter. In some examples, more than one future portion of the plot may be included, wherein both a predicted outcome element for the first activity item and a predicted outcome element for the no action condition are displayed.

As another example, a second time aligned graph of a blood pressure parameter may be included in the patient timeline GUI. The second time aligned graph may include a time aligned plot of blood pressures, in some examples plotting blood pressure values and in other examples plotting categories of blood pressures (e.g., hypertensive, normal, hypotensive). Predicted outcome elements for the blood pressure parameter, including an element corresponding to the first activity item and a representation for the no action condition, may be plotted as part of or adjacent to the time aligned plot of blood pressures.

Predicted outcome elements may be displayed for each parameter displayed as graphs within the timeline GUI. Which parameters are displayed may be changed via user inputs, for example via selection of a parameter in a drop-down menu. When a parameter is added to and/or removed from the patient timeline GUI, corresponding predicted outcome elements may be displayed in an interactive manner. In some examples, predicted outcomes may be generated for each parameter, displayed and not displayed. In this way, processing power may be reduced when interactively changing viewed parameters within the timeline GUI as predicted outcomes are already determined and may be displayed interactively.

In examples in which confidence levels of predicted outcomes are determined, elements indicating confidence levels may be displayed alongside the predicted outcome elements. Confidence levels may allow users to adequately judge the predicted outcomes determined by the algorithms for decision making purposes.

Optionally at 418, a decision support time aligned graph of trends and predicted outcomes based on the first activity recommendation for multiple parameters may be displayed within the timeline GUI. In response to user selection within a drop-down menu for plotted parameters, more than one parameter may be plotted in a time aligned graph. The multi-parameter graph may be displayed for decision support in which probabilities of various parameter outcomes are plotted. In some examples, the more than one parameter may include all available parameters when an "all" option is selected from the drop-down menu. In other examples, more than one individual parameter may be selected from the drop-down menu and the selected parameters may be plotted. The graph of trends may therefore include trends of selected parameters based on the processed patient data and representations of predicted outcomes based on the AI generated outcome predictions. In this way, the user may visualize predicted outcomes of multiple parameters based on the first activity item.

Figure 5:
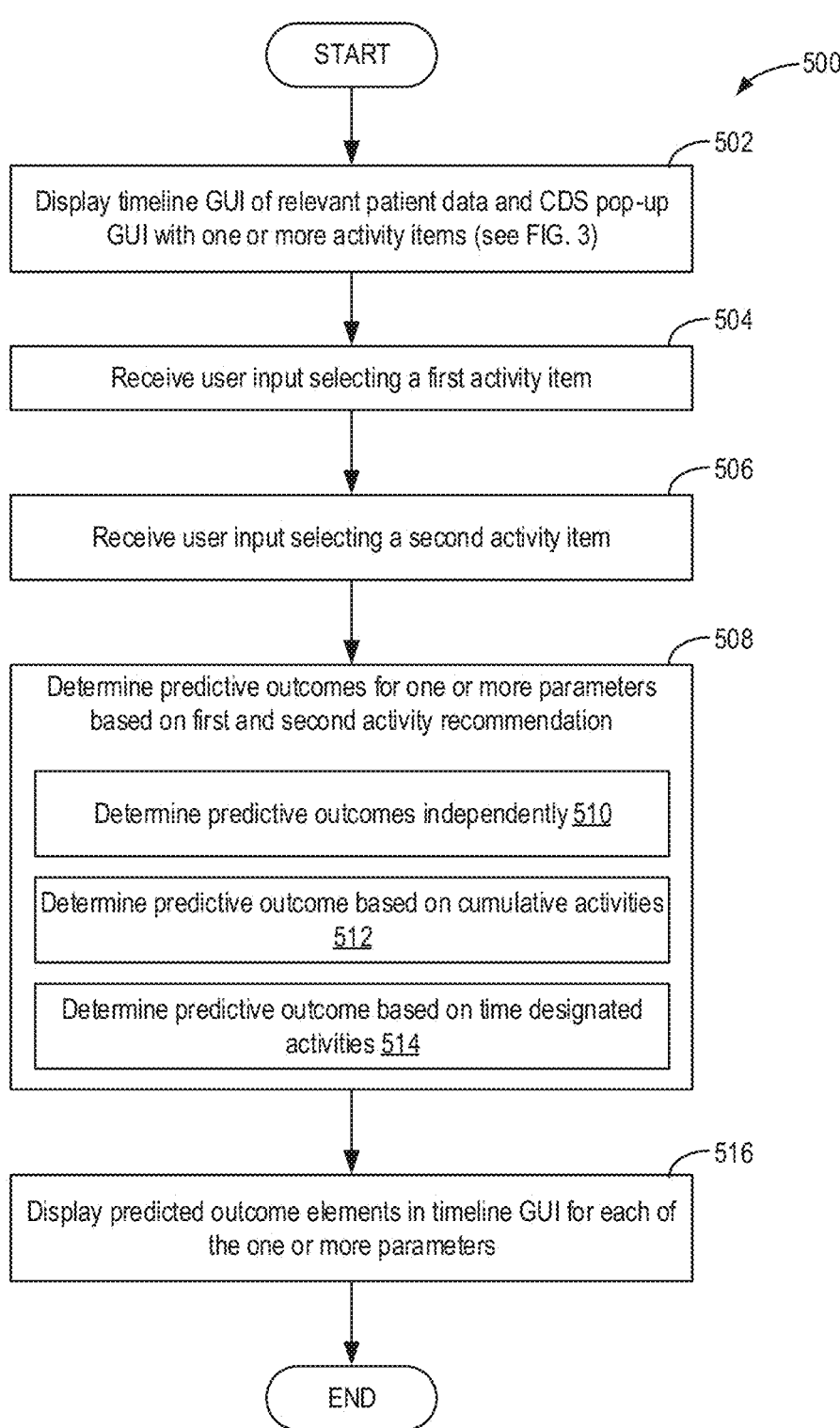
FIG. 5 is a flowchart illustrating a method for generating and displaying a predicted outcome of one or more parameters based on one or more selected activity items.

Turning now to FIG. 5, a flowchart illustrating a method 500 for determining predictive outcomes of one or more parameters based on more than one selected activity items is shown. Method 500 may be carried out according to instructions stored in memory of a computing device (e.g., memory 130 of presentation system 102 of FIG. 1), which may be executed by a processor of the computing device (e.g., processor(s) 132). While method 500 is described specific to one patient, at least portions of method 500 may be performed simultaneously for a plurality of patients. The method 500 will be described with respect to the systems of FIGS. 1-2, though it should be understood that similar methods may be performed via other systems.

At 502, a patient timeline GUI of relevant patient data and a clinical decision support GUI with one or more activity items displayed therein is displayed. As is described above with respect to FIG. 3, patient data may be obtained from one or more databases, including one or more EMRs, PACS, and the like. The patient data may then be processed to exclude data not relevant to a desired clinical setting. The processed patient data may be period segmented to time align data events in groups in a chronological manner. Based on the processed patient data, one or more activity recommendations may be determined, as will be further described with respect to FIG. 6.

Based on the period segmented processed patient data, the patient timeline GUI may be generated. The patient timeline GUI may display a plurality of time aligned graphs, history event panels, and more showing the processed patient data in a chronological manner. The patient timeline GUI may include one or more types of selectable elements that when hovered over and/or selected, launch various windows or perform actions. One of the selectable elements may launch the clinical decision support GUI as a side panel when selected. The clinical decision support GUI may display the one or more activity recommendations as activity items in a list. Pending activity items (e.g., activity items not yet accepted or rejected) may be displayed in a pending tab, accepted activity items may be displayed in a care plan tab, and completed activities may be displayed in a past activity tab.

At 504, user input selecting a first activity item is received. The first activity item may be selected from the clinical decision support GUI, in some examples from the pending tab and in other examples from the care plan tab.

At 506, user input selecting a second activity item is received. The second activity item may be selected from the clinical decision support GUI, in some examples from the pending tab and in other examples from the care plan tab. As an example, the first activity item may be selected from the care plan tab and the second activity item may be selected from the pending tab. While not specifically described here, in some examples, additional activities may be selected from the clinical decision support GUI as well.

At 508, predictive outcome(s) of one or more parameters are determined based on the first and second activity item. Determining the predictive outcome(s) of the one or more parameters may include applying one or more AI algorithms to the processed patient data. As is described with respect to FIG. 2, an algorithm determination module and a rules module may store instructions for the processor to execute to determine the algorithms to use to generate the predicted outcome(s) based on the processed patient data and the selected activity item.

The predicted outcomes may be determined independently for each selected activity/condition, as noted at 510. For example, each selected activity or condition (e.g., the no action condition) may be selected to generate a predicted outcome. The predicted outcomes may be generated and displayed independent of other selected activities/conditions. Further, each of the predicted outcome of the activities (e.g., the first and second activities) may be generated based on one or more algorithms independently. In this way, the user may visualize predicted outcomes of various activities in a comparative manner.

In other examples, the predicted outcomes may be determined based on cumulative activities, as noted at 512. For example, AI algorithms may determine predicted outcomes in the scenario in which both the first and second activity items are performed at the same time. The predicted outcomes may be determined by more than one algorithm, as determined by the algorithm determination and rules modules. In some examples, both independent predicted outcomes and a cumulative predicted outcome may be generated and displayed within the patient timeline GUI. In this way, the user may easily visualize various outcomes based on individual activities or groups of activities.

The predicted outcomes may be determined based on time designated activities, as noted at 514. For example, the first activity item may be designated to take effect at a first designated time and the second activity item may be designated to take effect at a second, later designated time. The predicted outcomes may be determined based on the scenario of the first activity item occurring at a designated time before the second activity item. Similar to as noted above, the predicted outcomes may be determined by more than one algorithm, as determined via the algorithm determination and rules modules.

In addition to determining predicted outcome(s) of the one or more parameters based on the first and second activity item, predicted outcomes may also be determined for the one or more parameters based on a no action condition, as described with respect to FIG. 4. The no action condition may indicate that no activity item is selected and algorithm(s) may determine a predicted outcome for each parameter in the condition that no changes are made to the patient's care. In some examples, one or more of the algorithms determined to generate the predicted outcome(s) for the first activity item may differ from one or more of the algorithms determined to generate the predicted outcome(s) for the no action condition.

In some examples, confidence levels of the determined predicted outcome(s) may be determined as well. The confidence levels may be determined based on corresponding algorithm(s) used to determine the predicted outcome(s). In some examples, confidence levels may be determined for both the first activity item as well as the no action condition. Confidence levels may be determined as percentages, decimals, or other value.

At 516, predicted outcome elements representing the predicted outcomes are displayed in the patient timeline GUI for each of the one or more parameters. In some examples, predicted outcome elements may be displayed in response to user selection of a decision support element within the patient timeline GUI or clinical decision support GUI. As described above, the patient timeline GUI may include time aligned graphs, event panels, etc., through which time aligned data of one or more parameters may be displayed. For example, a time aligned graph of an atrial fibrillation burden parameter may be included in the timeline GUI. A time aligned plot of the time aligned graph of atrial fibrillation burden may include a plurality of data points based on the processed patient data, wherein data points belong to a date as an x coordinate and a parameter sub-type as a y-coordinate, wherein the parameter sub-types, for the example parameter of atrial fibrillation burden, are no atrial fibrillation, paroxysmal, persistent, and permanent. The time aligned plot may include one or more future portions for future dates, wherein the predicted outcome elements are included in the future portions of the plot.

Representations of predicted outcomes may be displayed with each parameter displayed as graphs or panels within the timeline GUI. Which parameters are displayed may be changed via user inputs, for example via selection of a parameter in a drop-down menu. When a parameter is added to and/or removed from the timeline GUI, corresponding predicted outcomes may be displayed as representations thereof in an interactive manner. In some examples, predicted outcomes may be generated for each parameter, displayed and not displayed. In this way, processing power may be reduced when interactively changing viewed parameters within the timeline GUI as predicted outcomes are already determined and may be displayed interactively.

In examples in which confidence levels of predicted outcomes are determined, elements indicating confidence levels may be displayed alongside the predicted outcome elem. Confidence levels may allow users to adequately judge the predicted outcomes determined by the algorithms for decision making purposes.

Figure 6:
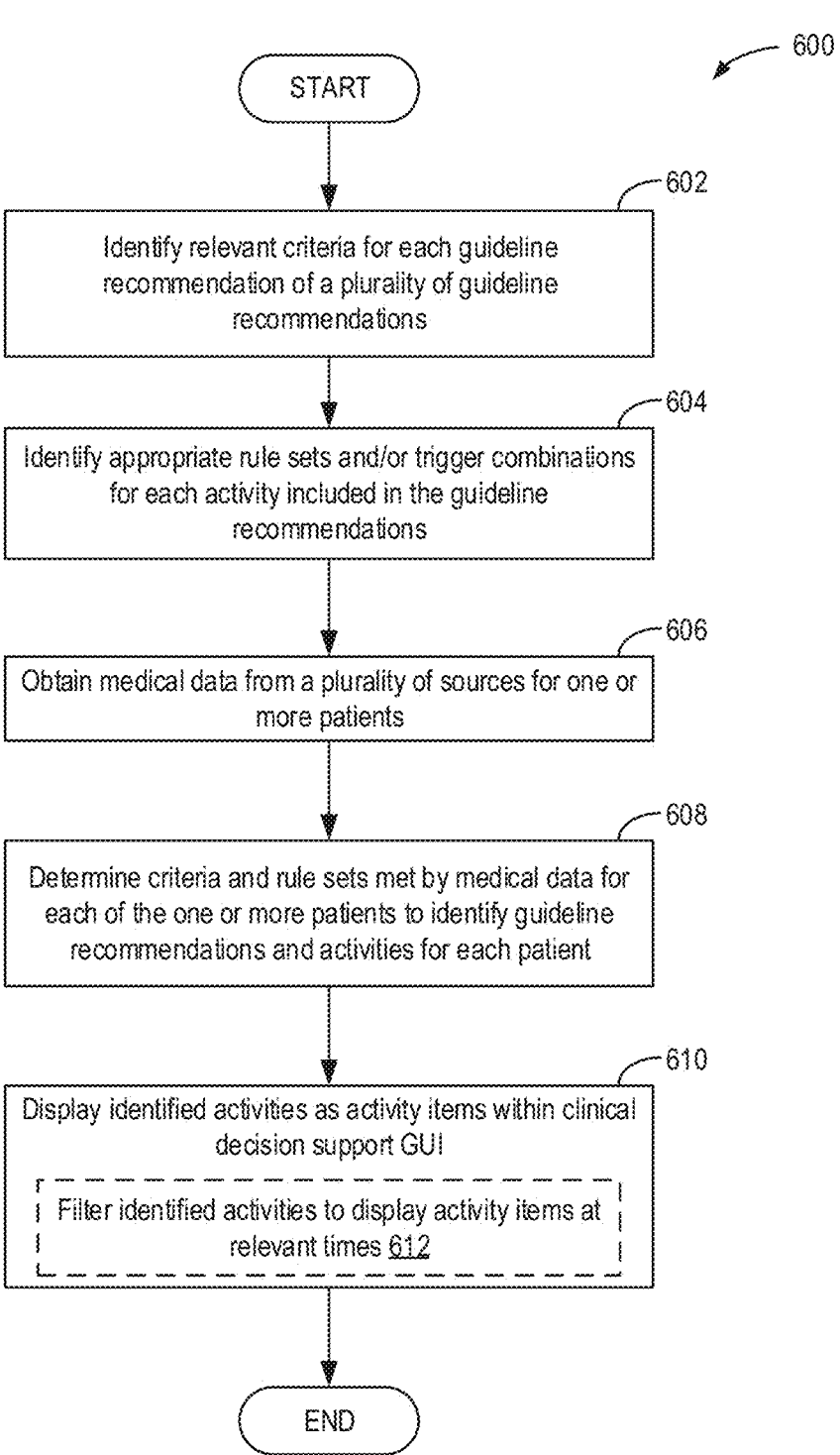
FIG. 6 is a flowchart illustrating a method for identifying activities for display within a clinical decision support GUI.

Turning now to FIG. 6, a flowchart illustrating an example method 600 for identifying activity items for display within a clinical decision support GUI is shown. In some examples, identification of activity items may occur in response to a user launching the clinical decision support GUI. In other examples, identification of activity items may occur in response to the user launching a patient timeline GUI. Determination/identification of activities for display may be based on decision trees defining triggers and rule sets, as will be described. Method 600 may be carried out according to instructions from a decision support module stored in memory of a computing device (e.g., memory 130 of presentation system 102 of FIG. 1), which may be executed by a processor of the computing device (e.g., processor(s) 132).

At 602, relevant criteria are identified for each guideline recommendation of a plurality of guideline recommendations. Guideline recommendations may be known to the system (e.g., sourced from, for example, ACC and/or ESC, and stored in memory). In some examples, identification of criteria (e.g., triggers) for each guideline recommendation may be automatic based on the known clinical guidelines. In other examples, identification of criteria for each guideline may be configured manually by a clinical expert or care provider and inputted into the system, as described with reference to FIG. 1. The criteria for each guideline recommendation may be data obtainable for a patient from one or more sources (e.g., past medical history information including prior diagnoses, prior imaging/pathology/ECG findings, prior laboratory results or vital signs, among others). Each trigger may be defined based on a procedure code stored in the memory and thus determination of whether a particular trigger has been met may be based on a procedure code within patient information (e.g., an EMR) matching a procedure code stored in memory as part of the criteria for guideline recommendations. As described above, each guideline recommendation may include one or more activities that may be recommended if the guideline recommendation is indicated.

At 604, appropriate rule sets and/or trigger combinations are identified for each activity of a set of activities included in the guideline recommendations. As noted, the criteria for each guideline recommendation may be a relatively large group of triggers possible to be met for a guideline recommendation to be indicated. Rule sets (e.g., trigger combinations) may be determined for each activity for relevant activities to be recommended for the patient. In this way, irrelevant or erroneous activity suggestions may be avoided. The rule sets and criteria for the guideline recommendations and activities may define one or more decision trees that are stored in memory.

For example, patient data may satisfy one trigger of a set of criteria for a guideline recommendation but not the other triggers in the set. Rule sets determined and included in a rules module of the system may dictate a combination of triggers that may be satisfied by the patient data in order for an activity to be indicated. Thus, the patient data does not indicate that the criteria for the guideline recommendation have been satisfied because only trigger (of more than one trigger of a rule set) has been satisfied. In this way, while patient data may include triggers for one or more guideline recommendations, with determination of appropriate rule sets of the set of activities and which of the rule sets the patient data satisfies, only the relevant activities will be displayed as activity items for the patient. Rule sets may be stored in memory as decision trees and a decision tree algorithm may be performed by the decision support module to determine which rule sets are met. In some examples, activities may have individual decision trees. In other examples, dependent upon the patient data obtained, larger decision trees may lead to multiple recommended activities.

At 606, medical data from a plurality of sources for one or more patients is obtained. The patient data may be obtained from EMR databases, an ECG management system, PACS, HIS/RIS/CIS, pathology systems, and more, as described previously with respect to FIG. 1. The medical data may include information of prior hospitalizations, pathology results, imaging exam findings, laboratory values, vital signs, medications, diagnosed conditions, ECG waveforms and/or findings, and more. The patient data may include dates corresponding to each datum. The patient data may include all available data from each of the plurality of sources and/or may be processed to filter out irrelevant data based on a desired setting (e.g., retaining data related to cardiology while filtering out other data). The patient data may be obtained in response to a request (e.g., a user input or selection) to display a timeline of patient information/past medical history or automatically in response to an application being launched.

At 608, criteria and rule set(s) met by medical data for each of the one or more patients are determined to identify guideline recommendations and activities indicated for each patient. As described, each guideline recommendations may have identified criteria and rule sets that may be met in order for the activities to be indicated for a patient. Medical data for each patient may be analyzed to identify criteria (e.g., triggers), for example, based on matching procedure codes as described with respect to FIG. 1. The identified criteria may then be analyzed to determine whether rule sets are met for each activity. If a rule set for an activity is met by medical data for a patient, the activity may be indicated for the patient and displayed as an activity item in a user interface. In this way, the user may be presented with clinically-based guidance that may increase efficiency and accuracy of clinical decisions, thereby improving patient care and clinical outcomes.

At 610, identified activities are displayed as activity items within a clinical decision support GUI. As described, the clinical decision support GUI may be displayed on top of or otherwise as part of a patient timeline GUI that displays the medical data obtained from the plurality of sources in a time arranged manner. The clinical decision support GUI may display each identified activity that is to either be accepted or rejected by a user via user input to the clinical decision support GUI, as previously described. Each identified activity may also be selected to generate predicted outcomes thereof.

In some examples, the identified activities are filtered to display activity items at relevant times, as noted at 612. For example, an activity may be identified for suggestion for a patient, but the activity may have already been suggested, accepted, and completed for the patient. In some examples, the activity may not be displayed as an activity item until a specified time frame has passed. In other examples, the activity may not be displayed as an activity item if it is determined to be an activity that may be suggested only once.

In some examples, one or more of the identified activities may be available for outcome prediction, as noted. If available, the clinical decision support GUI may include an outcome prediction element corresponding to an activity item that when selected generates predicted outcomes thereof as previously described.

Figure 7:
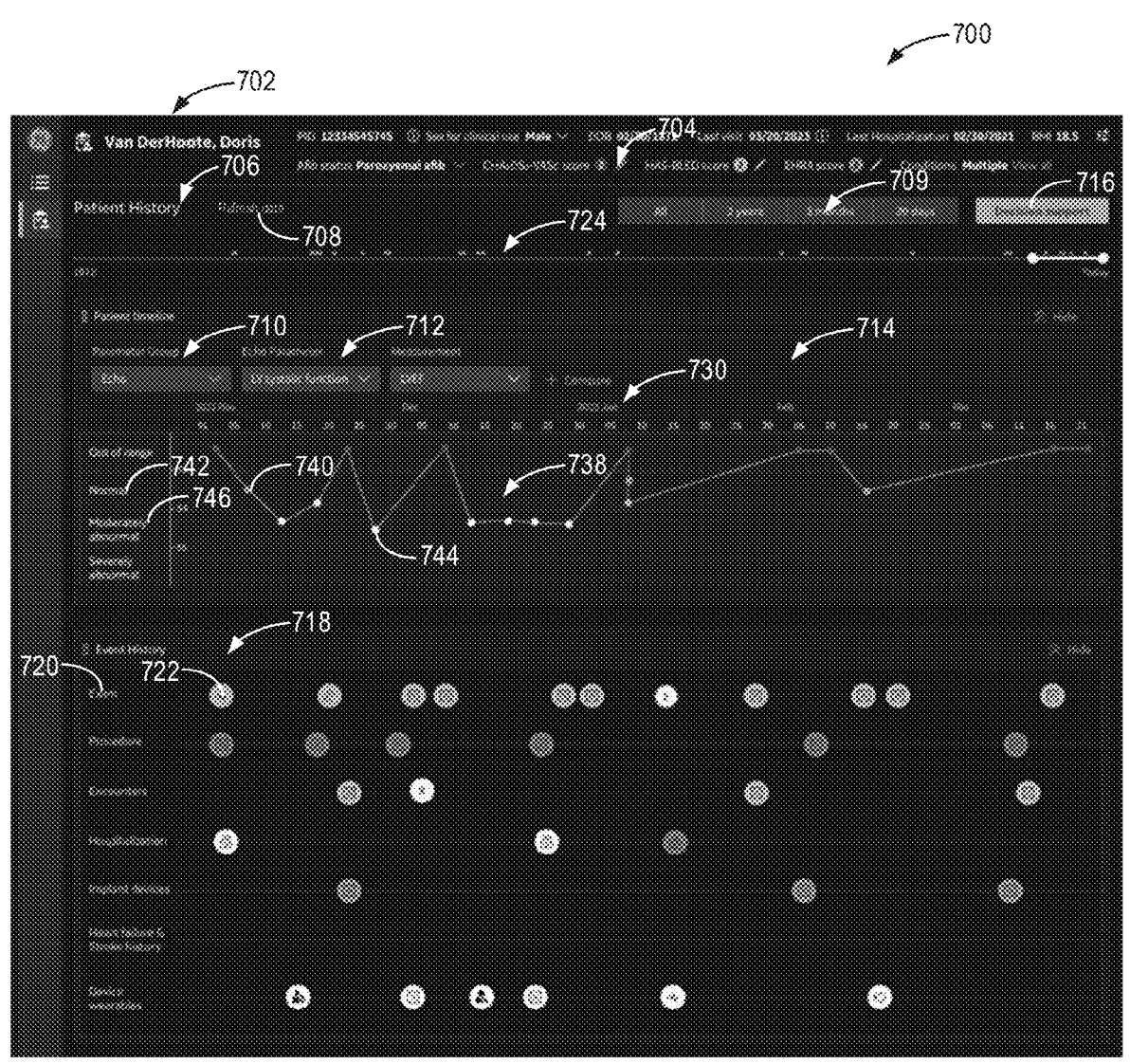
FIG. 7 shows an example patient timeline GUI generated with the system of FIG. 1.

Turning now to FIG. 7, an example of a patient timeline GUI 700 is shown that may be generated for a patient by presentation system 102. Patient timeline GUI 700 may be displayed on a display of a care provider device (e.g., user device 134 of FIG. 1) or another type of user device, such as a tablet or laptop computer. Patient timeline GUI 700 may include a plurality of different categories of timelines that may be displayed together or individually in a time-aligned manner as different panels of the patient timeline GUI 700. Data points and icons within each of the different panels may indicate or represent a plurality of history events and patient parameters retrieved from a plurality of data repositories (e.g., EMRs, PACS, etc.). Patient timeline GUI 700 may be accessed via a selectable link within one or more EMRs or may be a standalone application accessible by the computing device. The presentation system 102 by which information displayed within the patient timeline GUI 700 is generated may be patient centric, such that a link within an EMR may be specific to a patient and selection of the link may trigger display of information within the patient timeline GUI 700 relevant to that patient.

Patient timeline GUI 700 may include a patient information panel 702 that includes 1) a plurality of patient demographics including patient name, gender, date of birth, body mass index (BMI), last hospitalization, among others; 2) a plurality of clinical setting-specific data, for example for a cardiology clinical setting, the clinical setting-specific data may include atrial fibrillation status, a congestive heart failure-hypertension-age-diabetes-stroke-vascular disease (CHA$_2$DS$_2$-VASc) score, and a hypertension-abnormal renal/liver function-stroke-bleeding history or predisposition-labile international normalized ratio (INR)-elderly-drugs/alcohol concomitantly (HAS-BLED) score, among others; and/or 3) a date/time in which the data presented in the patient timeline GUI 700 was last updated. The patient information panel 702 may also include one or more selectable links 704 that when selected allow a user to input information regarding one or more of the data displayed in the patient information panel 702. In some examples, each of the one or more selectable links 704 corresponds to one of the presented demographics or clinical setting-specific data (or other datum included in the patient information panel 702). For example, a selectable link may correspond to a HAS-BLED score that allows the user to input a determined score.

The patient timeline GUI 700 may further include a patient history panel 706. The patient history panel 706 may include a patient history timeline 724, a time aligned graph 714, and an event history panel 718. The patient history timeline 724 may indicate from left to right dates of available data for the patient. The user may select via user input a range of years/dates on the patient history timeline 724 that is to be presented in the patient timeline GUI 700. Alternative to selecting a range of years/dates on the patient history timeline 724, the user may select one of a plurality of predefined ranges of dates 709 from which data may be pulled by the presentation system 102. Additionally in some examples, the patient history panel may include a refresh element 708 that when selected triggers resampling of patient data to update information displayed in the patient timeline GUI 700. In other examples, data may be continuously updated in real-time.

A parameter group menu 710 may be further included in the patient history panel 706 that allows the user to select what parameters are to be displayed in the time aligned graph 714 from a drop-down menu. For example, a clinical parameter group may be selected in order to display clinical parameters (e.g., diagnoses, conditions, encounters, etc.). Other parameter groups that may be selected include but are not limited to lab, ECG, imaging findings, and algorithmic scores. Each parameter group may include one or more parameter types and in some examples sub-types (e.g., measurements) that may be plotted on a time aligned graph. For example, an ECG parameter group may include a plurality of parameters found in an ECG, such as a QT interval, heart rate, etc. and an echocardiogram parameter group may include parameter types including various heart functions visualized by an echocardiogram exam and parameter sub-types may include various measurements for a chosen heart function.

A plotted menu 712 may be further included in the patient history panel 706 that allows the user to select which condition, lab value, vital sign, etc., is plotted on the time aligned graph 714. Options available in a drop-down menu of the plotted menu 712 may be determined/filtered based on which parameter group is selected in the parameter group menu 710. For example, for the clinical parameter group, options displayed in the plotted menu 712 may include conditions such as atrial fibrillation, strokes, cardiovascular events such as myocardial infarctions, and/or the like, but may exclude lab values, which may be options for a lab parameter group.

The time aligned graph 714 may display a condition, finding, laboratory test, algorithmic score, or other as based on the selected parameter from the plotted menu 712. The time aligned graph 714 may display one or more data points 738 in a chronological manner, each data point corresponding to a documented event relating to the plotted parameter. The parameter plotted on the time aligned graph 714 may include one or more headings and each data point included in the graph may correspond to one of the one or more headings. For example, for left ventricular ejection fraction as a plotted parameter sub-type measurement of an echocardiogram parameter, the one or more headings of the time aligned graph 714 may be status of left ventricular ejection fraction (e.g., out of range, normal, moderately abnormal, severely abnormal). Each of the data points may be subcategorized by the heading to which it corresponds. For example, a first data point 740 may correspond to a first heading 742 (e.g., normal left ventricular ejection fraction) for a first date while a second data point 744 may correspond to a second heading 746 (e.g., moderately abnormal left ventricular ejection fraction) for a second date.

In some examples, a timeline 730 of the time aligned graph 714 may include a range of dates specified by the patient history timeline 724 or by the plurality of predefined ranges of dates 709. The timeline 730 may be an abscissa of the time aligned graph 714 and the one or more headings may act as an ordinate of the graph. The event history panel 718 may also be time aligned according to the timeline 730. The event history panel 718 may include a plurality of types of events 720 including exams (e.g., non-invasive diagnostic exams), procedures, encounters, hospitalizations, disease/condition events (e.g., heart failure and stroke history), and/or other types of events. Each of the types of events 720 may include one or more event icons 722. Each of the event icons 722 may correspond to a date on the timeline 730.

In some examples, each of the event icons 722 of the event history panel 718 and the one or more data points 738 of the time aligned graph 714 may be selectable. When selected or hovered over, additional information regarding the event which a selected event icon represents may be displayed in a pop-up window.

While not shown in FIG. 7, in some examples, the patient timeline GUI 700 may include additional panels, including but not limited to a response to treatment visualization and a medication panel. The response to treatment visualization may include a panel showing, for example, a diagram or silhouette of a heart with treated vessels (e.g., vessels treated during a coronary artery bypass graft procedure) shown as circles. Alternatively, or additionally, response to treatment visualization may include textual information regarding changes in cardiac health status (e.g., in the form of cardiac risk scores or other statuses) prior to and following various treatments and/or interventions, including procedural, surgical, or medical (e.g., medication management). The medication panel may include relevant medication categories as headings and medication icons for each of the headings displayed with respect to time similar to the event history panel 718.

The patient timeline GUI 700 may further include a decision support element 716. The decision support element

716, when selected, may trigger the processor to execute instructions in a decision support module (e.g., decision support module 126 of FIG. 1) to generate or identify one or more activity items for the patient and may launch a clinical decision support GUI. The clinical decision support GUI may be a modification of the patient timeline GUI 700 whereby the clinical decision support GUI is displayed as a pop-up interface window or a side panel of the patient timeline GUI 700.

Thus, via patient timeline GUI 700, patient information relevant to the patient's condition (e.g., cardiology specific/cardiovascular condition) may be displayed in a time-ordered fashion. The patient information may be displayed via small graphical elements with minimal text, which may allow a large number of events, records, and reports to be included in the same timeline or graph. The user may select a graphical element of interest to view more information about the corresponding event, record, or report. The patient information may be stored in different databases that would otherwise be accessed via individual interfaces, and thus by aggregating the patient information via the patient timeline GUI 700, the amount of time demanded to review relevant patient information for diagnosis and treatment decisions, including time spent in review of guideline recommendations presented in a clinical decision support GUI, may be reduced.

The timelines disclosed herein aggregate patient data into a single place, e.g., into a single application, which helps reduce wasted time searching for known but scattered data, and unknown and missing data. The timelines reduce cognitive overloads and aid clinical thinking because the patient record data is reconstructed into a clinically helpful structure (co-morbidities complicates decision making). Care providers treating transfer patients or new patients can quickly get to diagnosis or treatment completion if such a simple multi-omic view is shown.

Figure 8:
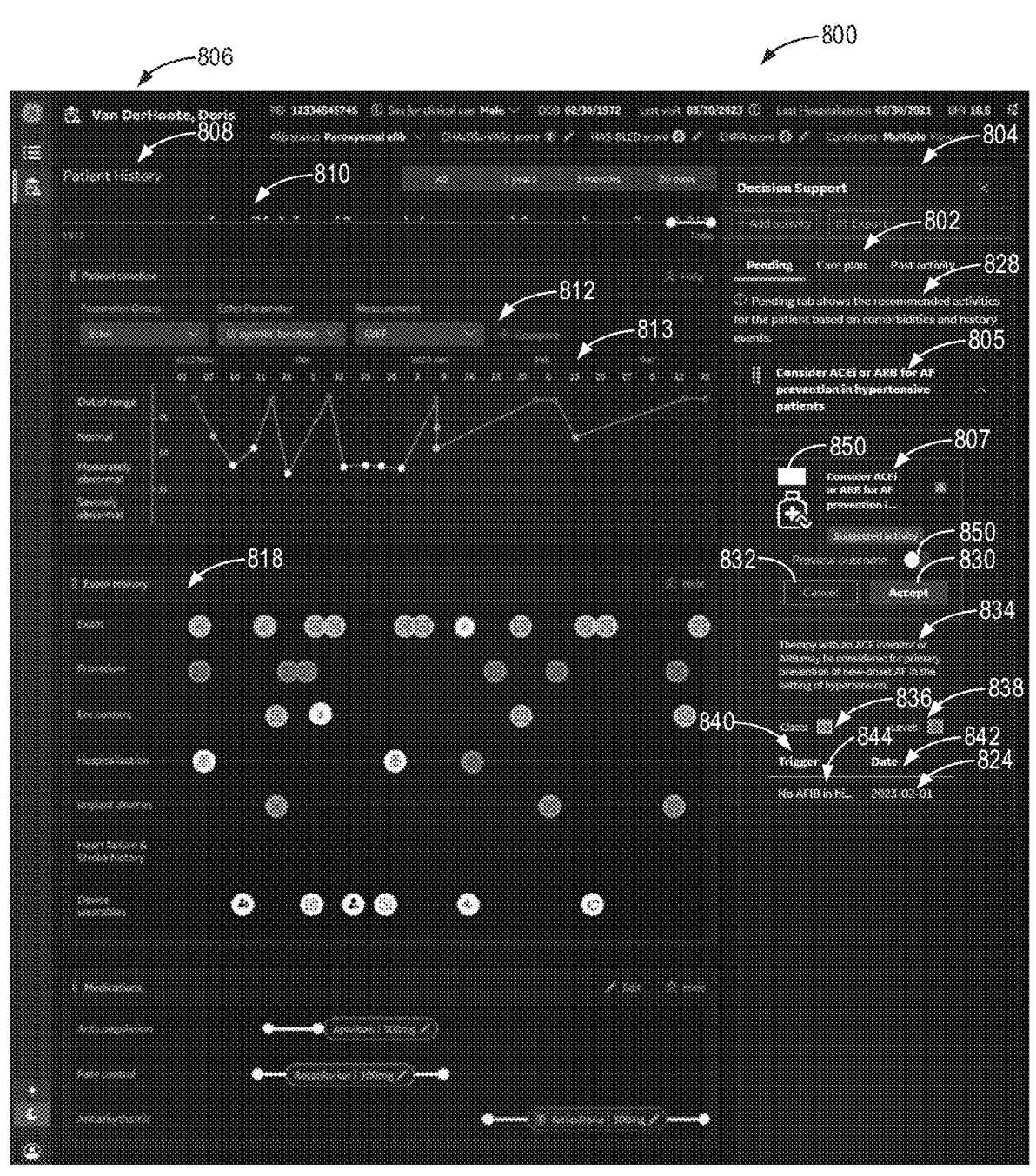
FIG. 8 shows an example patient timeline GUI with a clinical decision support GUI.

Turning now to FIG. 8, a second example of a patient timeline GUI 800 is shown. The patient timeline GUI 800 includes a clinical decision support GUI 804. Patient timeline GUI 800 may be displayed on a display device of a care provider device (e.g., user device 134 of FIG. 1) coupled to a patient information system (e.g., patient information system 100 of FIG. 1). The clinical decision support GUI 804 may be displayed as a side panel of the patient timeline GUI 800, as shown in FIG. 8, modifying a layout of the patient timeline GUI 800. Alternatively, the clinical decision support GUI 804 may be displayed as a separate pop-up window on top of the patient timeline GUI 800. In examples in which the clinical decision support GUI 804 is displayed as a separate pop-up window, a position of the clinical decision support GUI 804 may be changed via user input.

Panels and elements displayed within the patient timeline GUI 800, including a patient information panel 806, a patient history panel 808 that includes a time aligned graph 812 with a timeline 813, an event history panel 818, and other panels, and a patient history timeline 810 may be similar to as described with reference to patient timeline GUI 700 of FIG. 7.

The clinical decision support GUI 804 may be displayed in response to user selection of a decision support element of the patient timeline GUI 800. The clinical decision support GUI 804 may display one or more activity recommendations as activity items for consideration, in some examples by a care provider. The one or more activities may be based on or otherwise included in guideline recommendations (e.g., treatment or care recommendations) for a patient and display of an activity item for a patient may be based on a decision tree algorithm of rule sets stored in a rules module or other memory of the computing device. The activity item may be a suggested care measure (e.g., a suggested future care measure) such as a future intervention, future screening, or future treatment measure, like a medication, procedure, screening test, lifestyle intervention, and the like. The guideline recommendation indicated by a guideline recommendation panel 805 may aid the user (e.g., the care provider) in decision making for treatment based on the patient's past medical history as displayed within the patient timeline GUI 800.

The clinical decision support GUI 804 may include a menu 802 with a plurality of headings (e.g., tabs), including a pending tab, a care plan tab, and a past activity tab. The pending tab may display suggested activities yet to be interacted with. The care plan tab may display activities accepted by the care provider as well as information specific to the accepted activities, in some examples, including source information. Activities in the care plan may be considered future treatments, interventions, screenings, etc. yet to be completed. The past activity tab may display activities that have been completed and are therefore no longer included in the care plan.

When the pending tab is selected from the menu 802, clinical decision support GUI 804 may include an information panel 828 that includes a description of the selected tab and the guideline recommendation panel 805. The guideline recommendation panel 805 may include one or more pending activity items. In some examples, each of the one or more pending activity items may be displayed at the same time in unexpanded states, displaying a limited amount of information for each activity. In other examples, one of the one or more activity items may be displayed in an expanded state.

In some examples, the guideline recommendation panel 805 may include one or more selectable elements, including an accept element 830, a cancel element 832, and a predicted outcome element 850 for each displayed activity item. The accept element 830, when selected via user input, may trigger inclusion of a current activity item (e.g., activity 807 currently selected) in the care plan. The cancel element 832, when selected via user input, may trigger exclusion of the current activity item from the care plan. Selection of one of the accept element 830 or the cancel element 832 may also trigger display of a subsequent activity item or display of a notation indicating that no further pending activities are available. In some examples, the accept element 830 and cancel element 832 may be displayed when an activity is in an expanded state. As such, acceptance or rejection of the activity may trigger a subsequent activity to be displayed in an expanded state. In another example, acceptance or rejection of the activity may trigger the guideline recommendation panel 805 to display each remaining pending activity item in an unexpanded state and the user may then select which of the remaining pending activities to expand and interact with.

In some examples, selection of the predicted outcome element 850 of an activity item may be a user input that indicates that the activity item is to be considered when generating predicted outcomes. In this way, the predicted outcome element 850 may trigger generation of predicted outcomes for one or more parameters of the patient data based on one or more AI algorithms, as is described with respect to FIG. 4. In some examples, the predicted outcome element 850 may allow the user to designate a time in which the corresponding activity item. In this way, the user may designate times at which more than one activity item may be completed in order to generate a predicted outcome for the designated scenario. In some examples, selection of the predicted outcome element 850 may trigger display of predicted outcome element(s) within the timeline GUI that represent the predicted outcomes of the activity item. In other examples, selection of a separate element within the clinical decision support GUI 800 may trigger display of the predicted outcome element(s), for example in scenarios including selection of more than one activity item when generating predicted outcomes.

In some examples, rejection of an activity item may trigger an additional pop-up window through which the user may indicate a reason for rejection. The patient information system may record in memory the reason for rejection. Stored reasons for rejection may affect future activity recommendations generated by the system for the patient or other patients.

In some examples, the guideline recommendation panel 805 may further include a description of a reasoning for the activity 807 when the activity 807 is in the expanded state. As an example, an activity suggesting addition of an angiotensin converting-enzyme (ACE) inhibitor or an angiotensin receptor blocker (ARB) to a patient's medications may include a description 834 stating in text that the suggested therapy may be considered for prevention of new-onset atrial fibrillation in the setting of hypertension. A guideline recommendation indicated to trigger display of the activity may include criteria such as hypertension (e.g., historical values of elevated blood pressure readings or historical medication lists including one or more anti-hypertensives) and no prior documented history of atrial fibrillation, though others are possible. The description 834 may be specific to the activity displayed in an expanded state within the guideline recommendation panel 805. For example, when a second activity is displayed in an expanded state in response to user input for a first activity, the description 834 may change to match the second activity.

The guideline recommendation panel 805 may further include a guideline class 836 and a level 838 of the activity specific to the activity 807 being displayed within the guideline recommendation panel 805. The guideline class 836 may refer to a strength of the recommendation. For example, a class 1 guideline may be determined as strong, wherein the recommendation is considered effective/useful, while a class 2b may be considered weak, wherein the recommendation is considered potentially reasonable. Guideline classes may be predefined by a source from which the guideline recommendations were derived. The level 838 of the activity may be a confidence level or evidence level of the activity (e.g., activity 807). The confidence or evidence level may be based on number and type of triggers that were met to identify the activity for display. The confidence levels may also be predefined and stored in memory of the computing device.

In some examples, the guideline recommendation panel 805 may also include a trigger list 840 and a corresponding date list 842. Each trigger in the trigger list 840 may be one of the triggers or criteria of a rule set that was met by the patient data in order to display the activity 807 as a recommendation. Each date in the corresponding date list 842 may indicate a date of a corresponding trigger. For example, a trigger 844 of no atrial fibrillation in history may be found on a date 824.

Additionally, in some examples, the care plan may be exported to a connected EMR in order for accepted activities to be integrated into the EMR for action. For example, a care plan generated for a patient may include a new medication and a screening diagnostic exam. When exported back to the EMR, the new medication and the screening diagnostic exam may be added as orders for the patient, either automatically or via user selection of each care plan item.

In some examples, activity items displayed within the pending tab and/or the care plan tab may be selectable to trigger AI generated predicted outcomes for one or more parameters of the obtained patient data. The AI generated predicted outcomes may be based on the selected activity item and the patient data and may demonstrate a predicted trend, value, condition, etc. for each of the one or more parameters. The predicted outcomes may be predicted outcomes in the case that the selected activity were to be implemented. Representations of the predicted outcomes may be displayed within the timeline GUI 800, for example within a time aligned graph, as will be further described with respect to FIG. 9.

Figure 9:
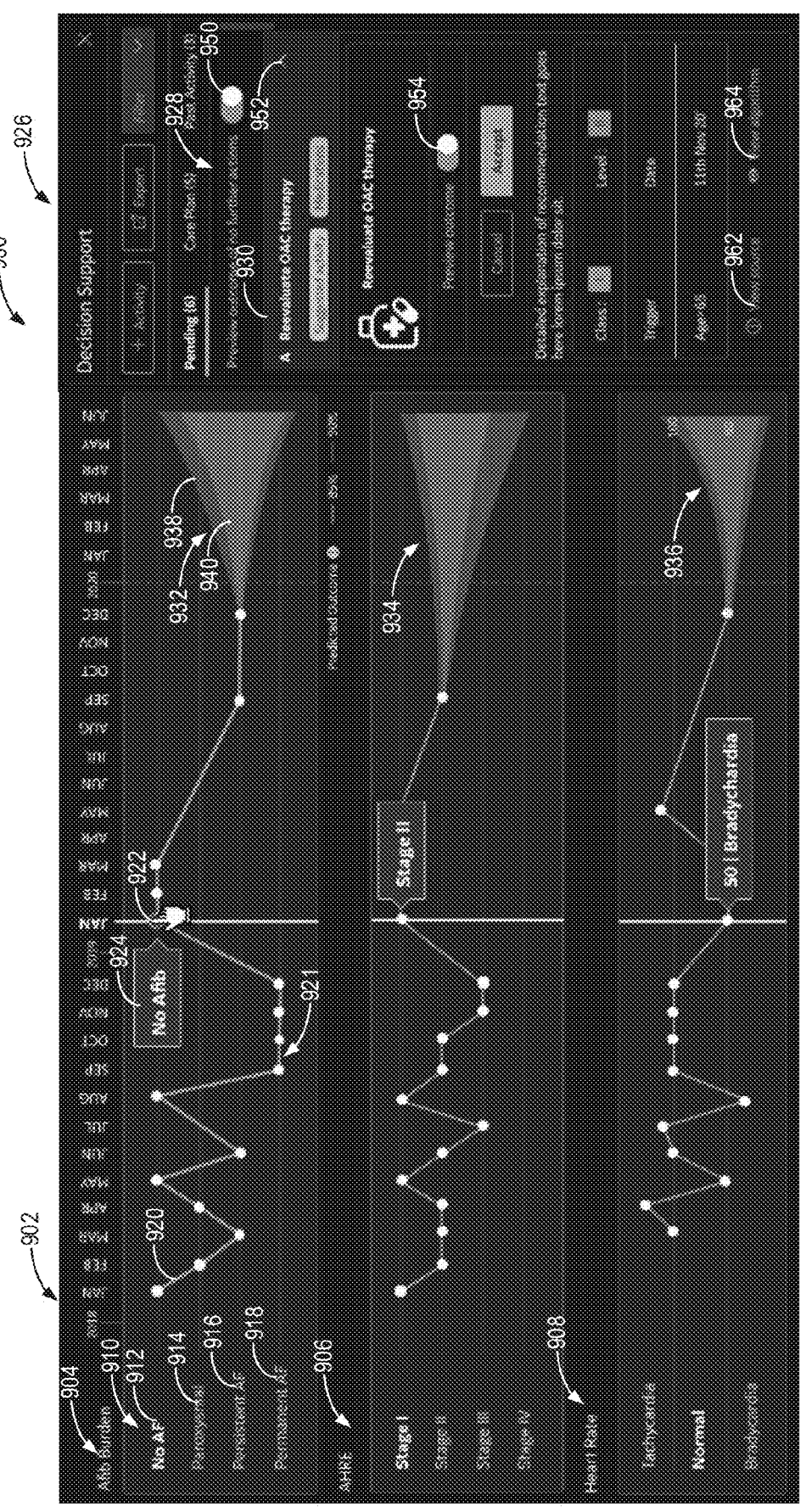
FIG. 9 shows an example patient timeline GUI with a clinical decision support GUI and multiple time aligned graphs.

Turning now to FIG. 9, a third example of a patient timeline GUI 900 is shown. The patient timeline GUI 900 includes a clinical decision support GUI 926, similar to the patient timeline GUI 800 described above. Patient timeline GUI 900 may be displayed on a display device of a care provider device (e.g., user device 134 of FIG. 1) or other user device coupled to a patient information system (e.g., patient information system 100 of FIG. 1). The clinical decision support GUI 926 may be displayed as a side panel of or other pop-up window on top of the patient timeline GUI 900.

The patient timeline GUI 900 may include plurality of time aligned graphs 902, such as a first time aligned graph 904, a second time aligned graph 906, and a third time aligned graph 908. Each of the time aligned graphs may display a respective parameter of patient data. As an example, the first time aligned graph 904 may correspond to an atrial fibrillation parameter, the second time aligned graph 906 may correspond to an atrial high rate event parameter, and the third time aligned graph 908 may correspond to a heart rate parameter. Each of the time aligned graphs may comprise a plot of a plurality of events as determined by patient data obtained from one or more sources. For example, the first time aligned graph 904 may comprise an ordinate of parameter subtypes 910, including a first subtype 912, a second subtype 914, a third subtype 916, and a fourth subtype 918. A plot 920 may be plotted from a plurality of events 921. Each of the plurality of events 921 may correspond to one of the subtypes shown in the ordinate. For example, an event 922 may correspond to the first subtype 912. Each of the plurality of events 921 may be selectable icons that when hovered over or selected via user inputs display a pop-up window of additional information regarding the selected event. For example, the event 922, when hovered over or selected, may trigger display of a pop-up window 924 that displays additional information regarding the event 922. The additional information, in some examples, may include the parameter subtype the event corresponds to, a date of the event, a value, a link to a corresponding exam (e.g., a link to an ECG tracing for an atrial fibrillation event), and/or the like. In some examples, different events when selected may display different types of information depending on the parameter and/or parameter subtype. For example, an event of a heart rate parameter may display parameter subtype, date, and heart rate value while an event of an algorithmic score may display a date, a score, and a link to a full algorithm questionnaire.

The clinical decision support GUI 926 may display one or more activity items 928, for example in a pending tab and/or a care plan tab, as previously described with respect to FIG.

8. The clinical decision support GUI 926 may also include a no action condition outcome prediction element 950. The no action condition outcome prediction element 950 when toggled to on via user inputs may trigger generation of a predicted outcome of one or more parameters if no further action is taken. When the no action condition outcome prediction element 950 is toggled to on (e.g., selected), predicted outcome elements representing the predicted outcomes of the one or more parameters based on the no action condition may be displayed in respective time aligned graphs. Further, each of the one or more activity items 928 may include prediction elements that are selectable to generate predicted outcomes of one or more parameters and display representations thereof on respective time aligned graphs. As an example, a first activity item 930, when expanded via an expansion element 952, may include a predicted outcome element 954. The predicted outcome element 954, when toggled to on or otherwise selected via user input, may trigger generation of predicted outcomes and display of elements representing the predicted outcomes within respective time aligned graphs. When more than one activity, or one or more activity items and the no action condition, are selected to generate predicted outcomes at the same time, the displayed elements in time aligned graphs may include future portions with predicted outcome elements for each of the selected activities, a cumulative predicted outcome, or a time designated predicted outcome.

In some examples, the clinical decision support GUI 900 may comprise a selectable element for turning outcome prediction on and/or off. If the selectable element is toggled to turn on outcome prediction, predicted outcome elements for available activity items and the no action condition may be displayed within the clinical decision support GUI 900. If the selectable element is toggled to turn off outcome prediction, predicted outcome elements for available activity items and the no action condition may not be displayed within the clinical decision support GUI 900.

For example, the patient timeline GUI 900 which includes the first, second, and third time aligned graphs 904, 906, and 908 of a first, second, and third parameter, respectively, may include a plurality of predicted outcome elements. For example, a first predicted outcome element 932 may correspond to the first time aligned graph 904, a second predicted outcome element 934 may correspond to the second time aligned graph 906, and a third predicted outcome element 936 may correspond to the third time aligned graph 908. Each of the first, second, and third predicted outcome elements 932, 934, and 936 may depict a predicted outcome for a corresponding parameter when an activity is carried out, such as the first activity item 930. When both the predicted outcome element 954 of the first activity item 930 and the no action condition outcome prediction element 950 are selected, the first predicted outcome element 932 may comprise a no action condition element 938 as well as an activity item condition representation 940. Both the no action condition element 938 and the activity item condition representation 940 may be displayed at the same time such that the user may compare outcomes of the no action condition and the activity item condition efficiently.

The clinical decision support GUI 900 may further include one or more selectable elements when the predicted outcome element of an activity item, such as the predicted outcome element 954 of the first activity item 930, is toggled on. For example, an algorithm element 964 may be displayed within the first activity item 930 when the first activity item 930 is expanded and the predicted outcome element 954 is selected. The algorithm element 964, when selected via user input, may launch a pop-up window displaying the one or more algorithms used to generate the predicted outcome(s) for the first activity item 930. Further, in some examples, the clinical decision support GUI 900 may display a source element 962 that is selectable to launch a pop-up window displaying one or more sources used to generate the activity. As is described above, clinical guidelines and rule sets may be obtained or otherwise derived from one or more sources, such as the ESC and/or the ACC.

As described, more than one time aligned plot may be displayed with respective values plotted over time. In this way, with predicted outcomes for a plurality of parameters displayed in respective time aligned graphs, the user may easily visualize patient data and potential effects of medical interventions on one or more parameters. As an example, for an activity item recommending addition of a diuretic medication such as furosemide, plots for parameters including blood pressure and renal function may display predicted outcome elements based on the activity item. The user may therefore see that addition of the diuretic medication for the patient may lower blood pressure, a desired effect, but may also decrease renal function, an undesired effect. With this information presented visually, the user, e.g., the care provider, may make an informed clinical decision about whether or not to add the diuretic medication to the patient's medication list. This may be particularly useful during high-demand situations or when patient data spans multiple years and multiple EMRs, making predicting the potential outcome of an intervention based on prior history more difficult for the care provider to assess manually.

Figure 10:
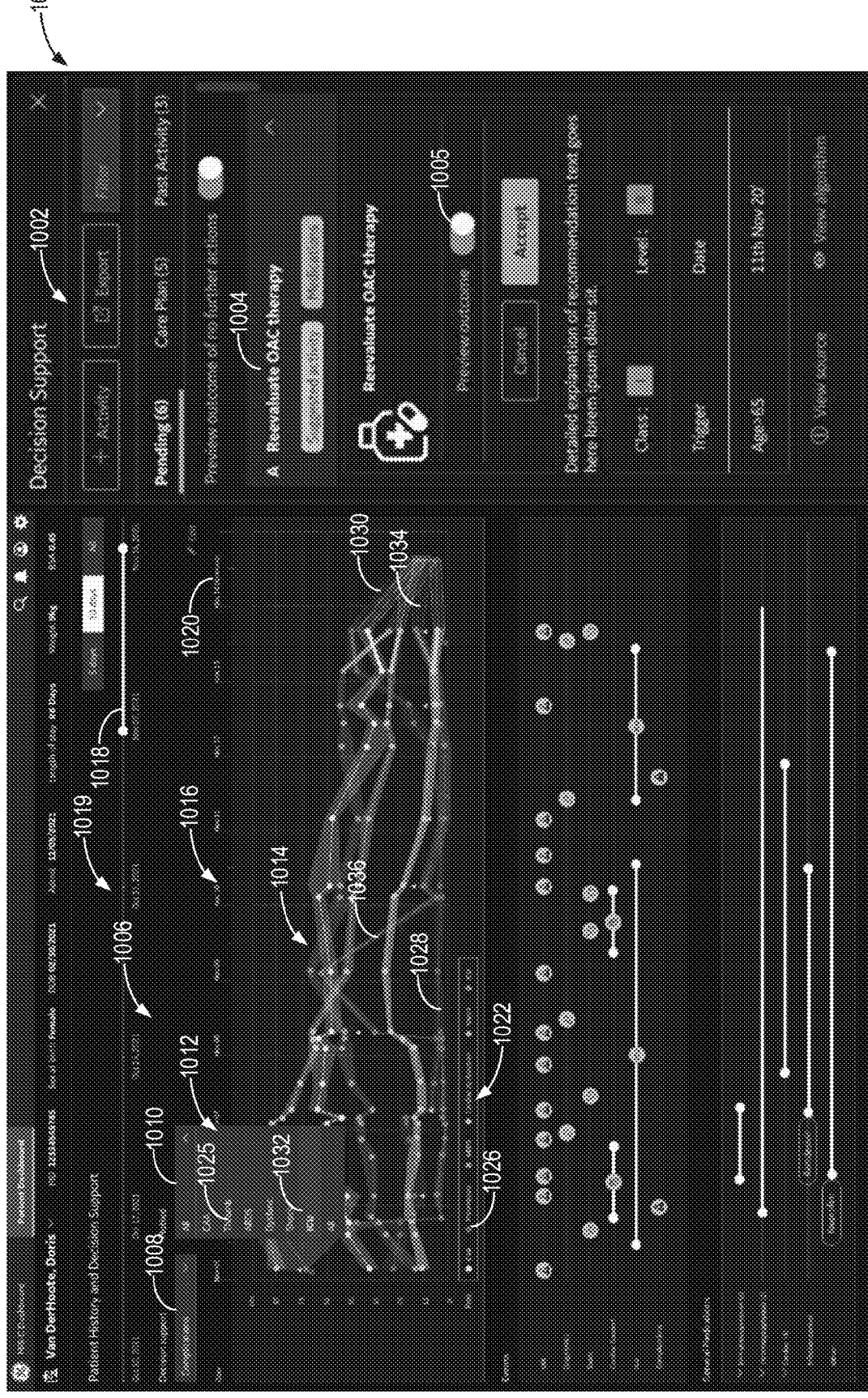
FIG. 10 shows an example patient timeline GUI with a multi-parameter time aligned graph.

Referring now to FIG. 10, a fourth example of a patient timeline GUI 1000 is shown. The patient timeline GUI 1000 includes a clinical decision support GUI 1002, similar to the patient timeline GUIs 800 and 900 described above. Patient timeline GUI 1000 may be displayed on a display device of a care provider device (e.g., user device 134 of FIG. 1) or other user device coupled to a patient information system (e.g., patient information system 100 of FIG. 1). The clinical decision support GUI 1002 may be displayed as a side panel of or other pop-up window on top of the patient timeline GUI 1000.

As is described previously, the clinical decision support GUI 1002 may comprise one or more activity items, including pending activity items and accepted activity items within a care plan, such as activity item 1004. When expanded, each activity item within the clinical decision support GUI 1002 may comprise a predicted outcome element that when selected triggers generation and display of predicted outcomes. For example, the activity item 1004 includes predicted outcome element 1005 that is toggled on (e.g., selected).

The patient timeline GUI 1000 may comprise a decision support time aligned graph 1006. The decision support time aligned graph 1006 may display data of one or more parameters. For example, a parameter type drop-down menu 1008 may allow a user to select from one or more available parameter types, such as labs, cardiac complications, and the like. A plotted parameter drop-down menu 1010 may display one or more parameters 1012 that are available from the selected parameter type of the parameter type drop-down menu 1008 to be plotted in the decision support time aligned graph 1006. As a non-limiting example, for a parameter type of "complications", available parameters displayed within the plotted parameter drop-down menu 1010 may include coronary artery aneurysm (CAA), thrombosis, acute respiratory distress syndrome (ARDS), cardiac dysfunction, shock, intensive care unit (ICU) (e.g., indicating that the corresponding patient demands ICU care), and/or an option for all the available parameters. Other parameter types may comprise various other available parameters.

The decision support time aligned graph 1006 may have an ordinate that indicates probability, in percentages, in some examples, with values ranging from 0 to 100. An abscissa 1016 of the decision support time aligned graph may be dates. A range of dates plotted for the abscissa 1016 may depend on a selected range 1018 of a timeline 1019 of the patient timeline GUI 1000. In some examples the selected range 1018 and therefore the abscissa 1016 may extend past a current date, for example into a future date 1020.

The decision support time aligned graph 1006 may display one or more plots 1014 based on selected parameter(s) from the plotted parameter drop-down menu 1010. A key 1022 may indicate which parameters are plotted on the decision support time aligned graph 1006, for example via the user of colors and parameter names. Each of the one or more plots 1014 may correspond to a depicted color of the key 1022. In examples in which an activity item from the clinical decision support GUI 1002 is selected for outcome prediction, one or more prediction plots may be included in the decision support time aligned graph 1006, for example aligning with the future date 1020.

Each of the one or more plots 1014 may comprise a plurality of data points, each data point corresponding to a particular event. Data points may be plotted based on respective dates and probabilities as obtained from the patient data. In some examples, the data points may be selectable elements that when hovered over or selected via user input may launch pop-up windows displaying additional information, such as dates/times, descriptions, and the like corresponding to the selected data points.

As an example, the option for all the available parameters may be selected from the plotted parameter drop-down menu 1010. The one or more plots 1014 of the decision support time aligned graph 1006 may therefore include plots for all the available parameters and the key 1022 may correspond thereto. For example, a first parameter 1025 may correspond to a first color 1026 of the key 1022. The first parameter 1025 may be plotted within the decision support time aligned graph 1006 as first plot 1028. The first plot 1028 may be displayed with the first color 1026. As noted, an outcome prediction may be generated for each of the plotted parameters. As such, the first plot 1028 may extend to the future date 1020 via a predicted outcome portion 1030 of the first plot 1028. Each of the other one or more plots of the decision support time aligned graph 1006 may similarly comprise predicted outcome portions of respective plots.

Similar to as described above, presenting multiple plots of various parameters within the same time aligned graph may allow the user (e.g., the care provider or patient in some examples) to easily visualize the potential effect of an intervention and/or no intervention on the one or more parameters all at once. In the example presented in FIG. 10, via the decision support time aligned graph, the user may easily visualize the predicted effect of selected activity item(s) on the plotted parameters. For example, probability of the first parameter 1025 (e.g., thrombosis) may decrease as an effect of the selected activity item 1004 and the probability of a second parameter 1032 (e.g., ICU) may be relatively unchanged as an effect of the selected activity item 1004, as noted by a predicted outcome portion 1034 of a second plot 1036 corresponding to the second parameter 1032.

In this way, data visualization and integration for clinical decision making may be more efficient. For example, a patient's medical history may indicate a predisposition to bleeding, but that information may be buried amongst a vast amount of other information. If that information is missed by a care provider manually searching the patient's vast medical history, a particular medication, such as an anticoagulant, may be added in error. The longitudinal cardiology patient history timeline system with predictive clinical decision support addresses this problem by sampling all available data repositories for relevant patient history data, presenting that data visually in a longitudinal (e.g., chronological) manner, generating one or more suggested care measures based on known clinical guidelines (e.g., displayed in the form of activity items), and generating predicted outcomes for one or more parameters. Therefore, the potential error of adding the anticoagulant to the patient with history of bleeding issues may mitigated without the care provider needing to spend undue amounts of time searching through medical history data prior to making a clinical decision.

Figure 11:
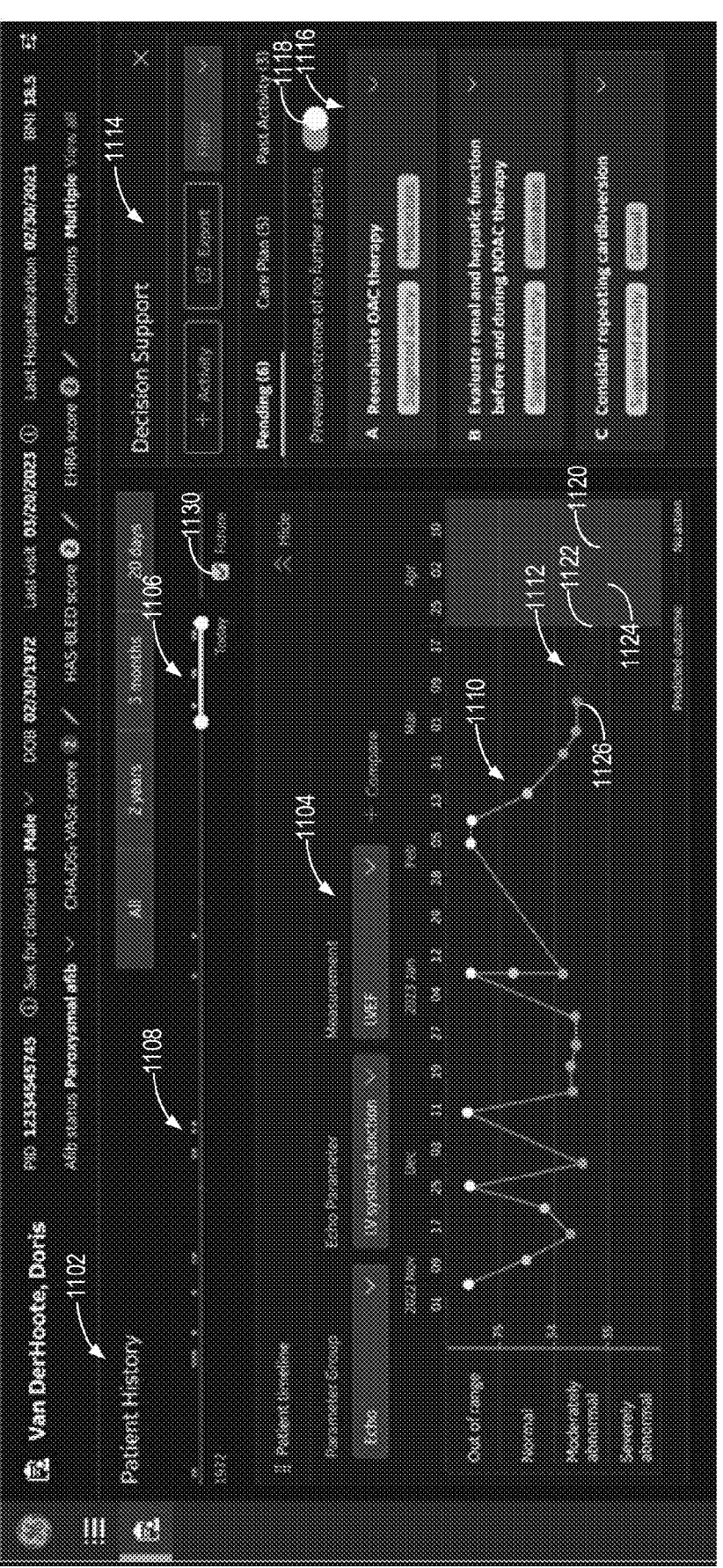
FIG. 11 shows an example patient timeline GUI with a no action condition predicted outcome element.

Turning now to FIG. 11, a fifth example patient timeline GUI 1100 is shown. The patient timeline GUI 1100 includes a clinical decision support GUI 1114, similar to the patient timeline GUIs 800, 900, and 1000 described above. Patient timeline GUI 1100 may be displayed on a display device of a care provider device (e.g., user device 134 of FIG. 1) or other user device coupled to a patient information system (e.g., patient information system 100 of FIG. 1). The clinical decision support GUI 1114 may be displayed as a side panel of or other pop-up window on top of the patient timeline GUI 1100.

Similar to as described previously, the clinical decision support GUI 1114 may comprise one or more activity items 1116. The one or more activity items 1116 may include pending activity recommendations displayed within a pending tab of the clinical decision support GUI 1114 as well as accepted activity items included within a care plan tab of the clinical decision support GUI 1114. As described previously, each of the one or more activity items 1116 may be expanded or unexpanded. When expanded, predicted outcome elements may be displayed for respective activity items. When unexpanded, the predicted outcome elements may not be displayed, as is show in clinical decision support GUI 1114. Also as previously described, the clinical decision support GUI 1114 may comprise a no action condition outcome prediction element 1118. When toggled on (e.g., selected), the no action condition outcome prediction element 1118 may trigger generation of a predicted outcome of one or more parameters based on the no action condition as well as display of a predicted outcome element within corresponding time aligned graphs.

For example, the patient timeline GUI 1100 may comprise a patient history panel 1102 comprising a time aligned graph 1104. The time aligned graph 1104 may display data of a selected parameter, similar to as described with respect to FIG. 7. A plot 1110 comprising a plurality of data points may be included in the time aligned graph 1104, each data point corresponding to a date and a heading. Each of the headings may correspond to the selected parameter, for example the headings may be various statuses, descriptions, or categories of the selected parameter. The dates available to the time aligned graph 1104 may correspond to a selected time range 1106 of a timeline 1108 of the patient timeline GUI 1100.

The plot 1110 may comprise a future portion 1112 including a predicted outcome element corresponding to a selected activity or condition from the clinical decision support GUI 1114. For example, the no action condition outcome prediction element 1118 may be selected and the future portion 1112 of the plot 1110 may correspond to the predicted outcome of the no further action condition. The future portion 1112 may comprise a predicted data point 1120 that corresponds to a date. The date to which the predicted data point 1120 corresponds may be based on a selected future timeline. The future timeline may be displayed when a future element 1130 is selected. The future portion 1112 of the plot 1110 may further comprise a plot line 1122 and a prediction window 1124. The plot line 1122 may connect a most recent data point 1126 of the plot 1110 to the predicted data point 1120. The prediction window 1124 may be a shaded region that indicates a possible outcome spectrum.

In some examples, the future portion 1112 of the plot 1110 may be shaded to represent improvement, stability, or decline. For example, in the patient timeline GUI 1100 presented in FIG. 11, the plotted parameter is left ventricular ejection fraction as determined from an echocardiogram. The headings of the time aligned graph 1104 include out of range, normal, moderately abnormal, and severely abnormal, with moderately abnormal being worse than normal and severely abnormal being worse than moderately abnormal. In some examples, the future portion 1112 may be shaded red if the predicted outcome is a decline (e.g., the predicted data point 1120 corresponds to a worse heading than the most recent data point 1126), as is shown in FIG. 11. In other examples, the future portion 1112 may be shaded orange if the predicted outcome is stable compared to the most recent data point 1126, yellow if the predicted outcome is improving by one heading compared to the most recent data point 1126, or green if the predicted outcome is improving by more than one heading compared to the most recent data point 1126. Other colors and designations are possible, however.

The future portion 1112 when corresponding to the no action condition may be considered a baseline trend. The baseline trend may indicate a predicted trend of the parameter if no further actions or interventions are taken. In this way, the user may be able to visualize a projected or predicted trend for the displayed parameter. Further, the plotted parameter may be changed via user inputs and future portions of resulting time aligned graphs for the different parameter(s) may be displayed based on the selected predicted outcome elements of the clinical decision GUI 1114. For example, the plotted parameter may be changed from left ventricular ejection fraction to atrial fibrillation. The plot of the time aligned graph may update to show data points of the atrial fibrillation parameter. In some examples, selection of an outcome prediction element, for example the no action condition outcome prediction element 1118, may trigger generation of a predicted outcome for multiple parameters, plotted and not plotted. In other examples, selection of the outcome prediction element may trigger generation of a predicted outcome for one or more plotted parameters. In such examples, changing which parameter is plotted may trigger generation of a predicted outcome of the new plotted parameter based on the corresponding activity or condition (e.g., the no action condition). In this way, via user inputs to the patient timeline GUI 1100, the user may easily visualize various predicted outcomes of an activity/condition, increasing efficiency and accuracy of clinical decision making.

In some examples, more than one future portion may be displayed in examples in which more than one activity is selected to generated predicted outcomes independent of one another. As described with respect to method 500, predictive outcomes for one or more parameters may be determined based on more than one activity with the more than one activity treated independently, cumulatively, or as time designated activities.

Figure 12:
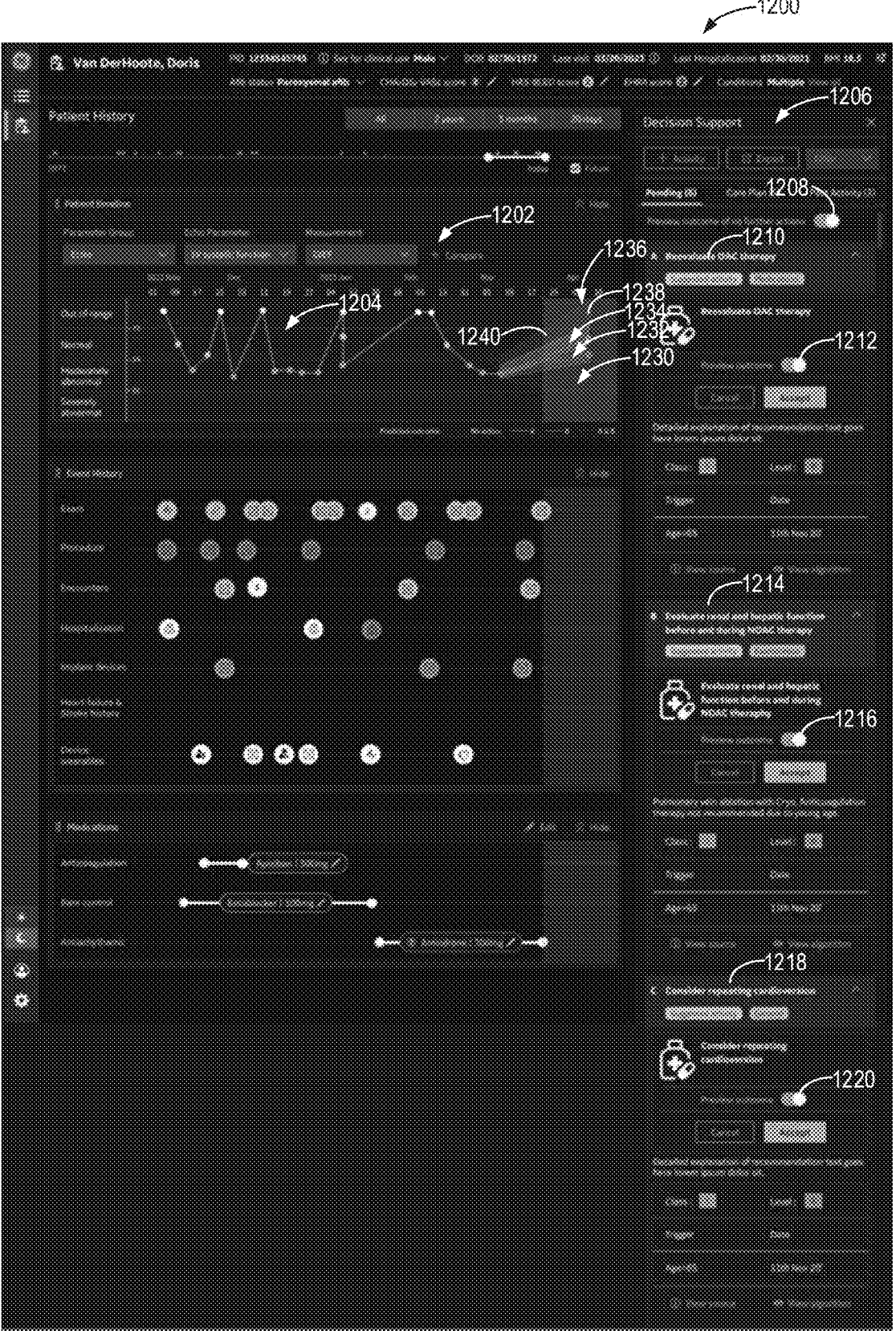
FIG. 12 shows an example patient timeline GUI with multiple activity item predicted outcome elements.

Turning now to FIG. 12, an example patient timeline GUI 1200 is shown demonstrating multiple future portions of a plot of a time aligned graph. The patient timeline GUI 1200 includes a clinical decision support GUI 1206, similar to the patient timeline GUIs 800, 900, 1000, and 1100 described above. Patient timeline GUI 1200 may be displayed on a display device of a care provider device (e.g., user device 134 of FIG. 1) or other user device coupled to a patient information system (e.g., patient information system 100 of FIG. 1). The clinical decision support GUI 1206 may be displayed as a side panel of or other pop-up window on top of the patient timeline GUI 1200.

The patient timeline GUI 1200, similar to the patient timeline GUIs discussed above, may comprise a time aligned graph 1202 displaying longitudinally organized patient data of a chosen parameter or group of parameters. The time aligned graph 1202 may comprise a plot 1204 comprising a plurality of data points. Each data point may correspond to a respective date and heading of the parameter or group of parameters. For example, as is previously described, a parameter may be echocardiogram, with an echocardiogram parameter type of left ventricular systolic function and a measurement type of left ventricular ejection fraction. Data points may be plotted along the plot 1204 for headings corresponding to measurements of left ventricular ejection fraction, including out of range, normal, moderately abnormal, and/or severely abnormal.

The clinical decision support GUI 1206, similar to as previously described, may display one or more activity items, such as first activity item 1210, second activity item 1214, and third activity item 1218. Each of the one or more activity items may be displayed in an unexpanded or an expanded state, as is show in FIG. 12. In some examples, each of the activity items may include an outcome prediction element. For example, the first activity item 1210 includes a first outcome prediction element 1212, the second activity item 1214 includes a second outcome prediction element 1216, and the third activity item 1218 includes a third outcome prediction element 1220. In other examples, one or more of the one or more activity items may not include a outcome prediction element in instances in which algorithms are not available to generate a predicted outcome for a given activity item. The clinical decision support GUI 1206 may also comprise a no action condition outcome prediction element 1208.

Each of the outcome prediction elements displayed within the clinical decision support GUI 1206 may generate a predicted outcome for one or more parameters (e.g., the parameter plotted in the time aligned graph 1202) for a given activity item or group of activity items. In some examples, as described with respect to FIG. 5, a predicted outcome generated may be based on cumulative activity items, wherein the predicted outcome describes a predicted trend for the parameter(s) if the corresponding activities were to take place at the same time. In other examples, also as described with respect to FIG. 5, a predicted outcome generated may be based on time designated activity items, where each activity item has a designated time at which it will occur in a particular scenario. For both cumulative and time designated scenarios, one future portion of the plot may be displayed in the time aligned graph for the activity items with a second future potion of the plot displayed if the no action condition predicted outcome element is also selected. In yet further examples, as is depicted in FIG. 12, predicted outcomes or the parameter(s) may be generated for each selected activity item and the no action condition independently.

In the example presented in the patient timeline GUI 1200, the first activity item 1210 may correspond to a first future portion 1236, the second activity item 1214 may correspond to a second future portion 1234, the third activity item 1218 may correspond to a third future portion 1232, and the no action condition may correspond to a fourth future portion 1230. Each future portion may comprise a predicted data point and a shaded window, as is previously described. For example, the first future portion 1236 may comprise predicted data point 1238 and shaded window 1240 similar to as described with respect to FIG. 11.

Each of the future portions of the plot 1204 may have a specified color based on a determined trend status. For example, future portions that are determined to decline with respect to status of the parameter may be displayed with a first color, such as red. Future portions that are determined to be stable with respect to status of the parameter may be displayed with a second color, such as orange. Future portions that are determined to improve a first amount (e.g., improve by one status) with respect to the status of the plotted parameter may be displayed with a third color, such as yellow. Future portions that are determined to image a second amount (e.g., improve by more than one status) with respect to the status of the plotted parameter may be displayed with a fourth color, such as green. In this way, the user may easily visualize projected trends of various activities with relation to a most current data point and more efficiently determine which activity to perform.

Figure 13:
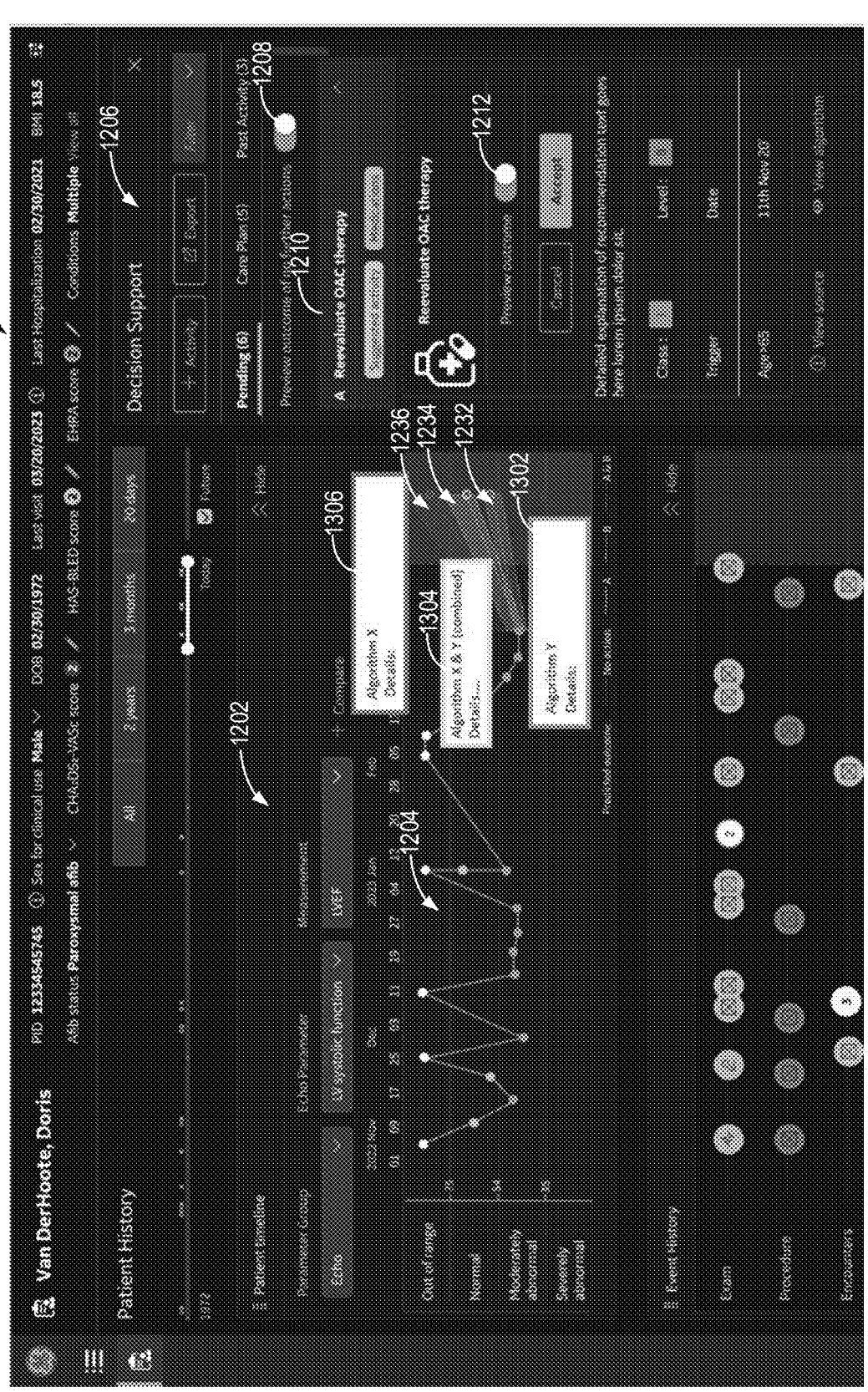
FIG. 13 shows the patient timeline GUI of FIG. 12 with additional pop-up windows.

Further, each of the shaded windows may be selectable via hovering or clicks to launch respective pop-up windows detailing additional information of a corresponding predicted outcome, including algorithm(s) used to generate the predicted outcome. In FIG. 13, the patient timeline GUI 1200 is shown with such pop-up windows.

For example, the first future portion 1236 of the plot 1204 may be selected, such as via a hover input, to display a first pop-up window 1306. The first pop-up window 1306 may be displayed as an overlay on top of the patient timeline GUI 1200. The first pop-up window 1306 may display details corresponding to the first activity item 1210 to which the first future portion 1236 corresponds. For example, the first pop-up window 1306 may display names and/or sources of one or more algorithms used to generate the predicted outcome represented by the future portion 1236. In some examples, the first pop-up window 1306 may also display a predicted status of the parameter (e.g., a heading to which a predicted data point corresponds).

In this way, each of the displayed future portions of the plot 1204 may be selectable to launch respective pop-up windows detailing corresponding information related to the predictive outcome and/or activity item. In some examples, one pop-up window may be displayed at a time. In such examples, hovering over a first future portion may launch a corresponding first pop-up window detailing information of a first predicted outcome of a first activity item. Then, hovering over a second future portion may trigger closing of the first pop-up window and launching of a second pop-up window detailing information of a second predicted outcome of a second activity item.

In other examples, more than on pop-up window may be displayed at a time. For example, the first pop-up window 1306 may be displayed in response to selection of the first future portion 1236, a second pop-up window 1304 may be displayed in response to selection of the second future portion 1234, and a third pop-up window 1302 may be displayed in response to selection of the third future portion 1232. Each of the first, second, and third pop-up windows may be displayed with a color corresponding to a color of the future portion to which it corresponds. For example, the first future portion 1236 may be displayed as a first color, such as green, and as such the first pop-up window 1306 may be displayed with the first color (e.g., shaded as the first color, with a border of the first color, etc.). Displaying the pop-up window with the color of its corresponding future portion may allow the user to more easily visualize which pop-up window corresponds to which future portion.

Figure 14:
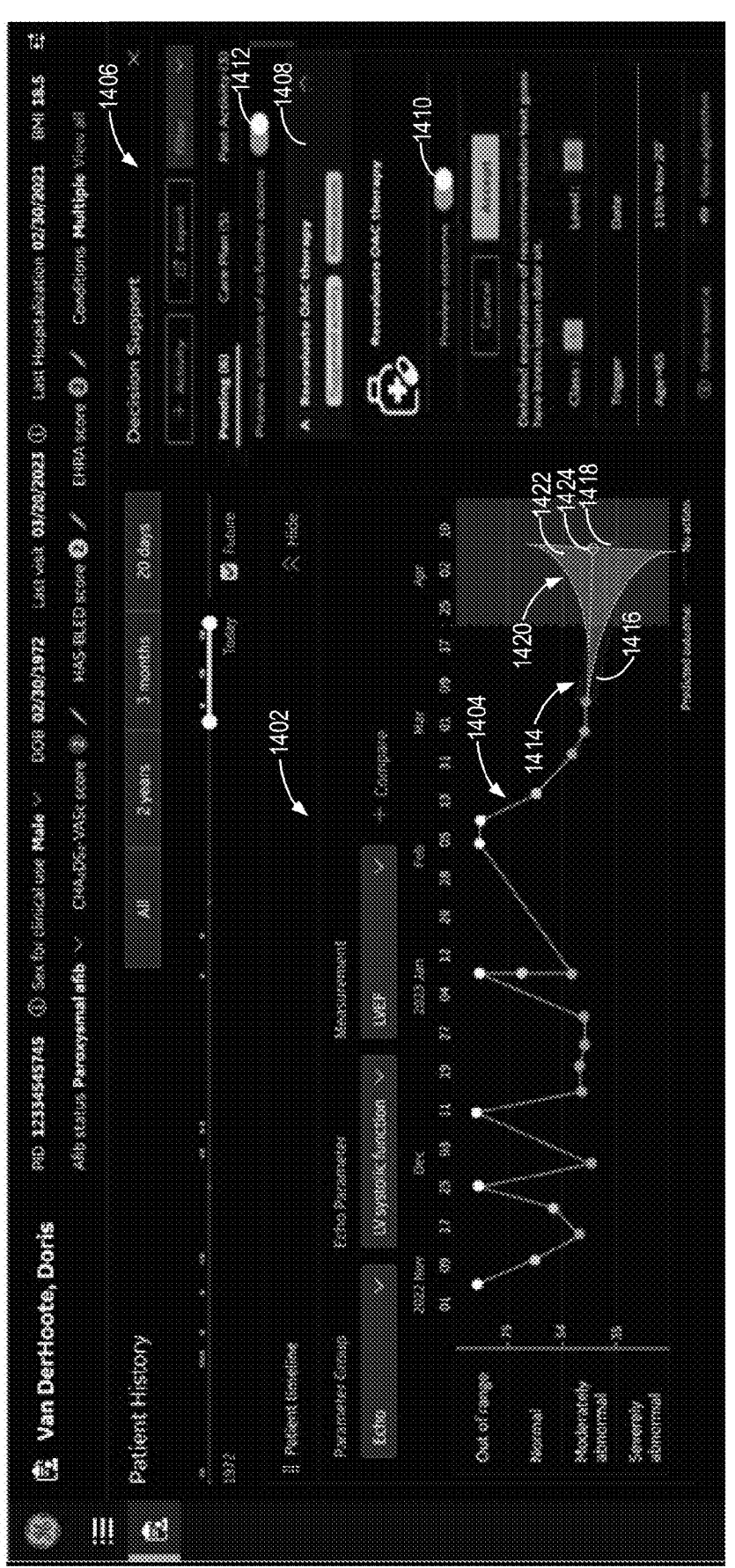
FIG. 14 shows an example patient timeline GUI with multiple predicted outcome elements.

FIG. 14 shows an example patient timeline GUI 1400 that includes a plurality of predicted outcome elements within a time aligned graph 1402. The patient timeline GUI 1400 includes a clinical decision support GUI 1406, similar to the patient timeline GUIs 800, 900, 1000, 1100, and 1200 described above. Patient timeline GUI 1400 may be displayed on a display device of a care provider device (e.g., user device 134 of FIG. 1) or other user device coupled to a patient information system (e.g., patient information system 100 of FIG. 1). The clinical decision support GUI 1406 may be displayed as a side panel of or other pop-up window on top of the patient timeline GUI 1400. Patient timeline GUI 1400 may be configured as patient-oriented or clinician-oriented, as previously described.

The time aligned graph 1402 may comprise a plot 1404. The plot 1404 may comprise a plurality of data points according to date and status of a chosen parameter plotted within the time aligned graph 1402, similar to as previously described. While FIG. 14 shows only one time aligned graph, it should be understood that more than one time aligned graph may be included in the patient timeline GUI 1400, each plotting a different parameter.

The clinical decision support GUI 1406 may be displayed as a pop-up window, side panel, or other of the patient timeline GUI 1400, as previously described. The clinical decision support GUI 1406 may comprise one or more activity items detailing various determined activity recommendations. Pending activity recommendations may be displayed as items within a pending tab and accepted activity recommendations may be displayed as items within a care plan tab. As an example, the clinical decision support GUI 1406 may include an activity item 1408. The activity item 1408 may include an outcome prediction element 1410 that when toggled on or otherwise selected triggers identification of one or more first algorithms, generation of a predicted outcome of the activity item 1408 based on the one or more first algorithms, and display of a first predicted outcome element 1420 within the time aligned graph 1402. The first predicted outcome element 1420 may be included as a future portion of the plot 1404 aligned with future dates.

The clinical decision support GUI 1406 may also include a no action condition outcome prediction element 1412. When toggled on or otherwise selected, the no action condition outcome prediction element 1412 may trigger identification of one or more second algorithms, generation of a no action predicted outcome based on the one or more second algorithms, and display of a no action predicted outcome element 1414 within the time aligned graph 1402.

In some examples, the first predicted outcome element 1420 may comprise a shaded predicted window 1422 and a predicted data point 1424. The predicted window 1422 may indicate a range of possible outcomes and the predicted data point 1424 may indicate a most likely predicted outcome amongst the predicted window 1422. Similarly, the no action predicted outcome element 1414 may comprise a shaded predicted window 1416 and a predicted data point 1418, wherein the predicted window 1416 indicates a range of possible outcomes and the predicted data point 1418 indicates a most likely predicted outcome amongst the predicted window 1416.

In some examples, the predicted window 1416 of the no action predicted outcome element 1414 may overlap with the predicted window 1422 of the first predicted outcome element 1420 in instances in which the ranges of predicted outcomes for the no action condition and the activity item overlap. The time aligned graph 1402 may display both predicted windows at the same time such that the user may easily and efficiently visualize the predicted outcomes of both the no action condition and the activity item to aid in clinical decision making.

In some examples, the range of possible outcomes for one activity/condition may be greater than another. For example, as shown in FIG. 14, the predicted window 1422 corresponding to the activity item 1408 may indicate a wider range of possible outcomes than the predicted window 1416 corresponding to the no action condition. In this way, the predicted window 1422 may indicate that executing the activity item 1408 may result in a more favorable outcome than the no action condition, but it may also result in a less favorable outcome than the no action condition. In this way, the patient timeline GUI 1400 may display patient data in a longitudinal manner within the time aligned graph 1402 and may also display to the user potential outcomes of various courses of action at the same time within a limited display window, allowing the user to more efficiently make informed clinical decisions for the patient.

Figure 15:
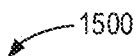
FIG. 15 shows an example patient timeline GUI with independent and cumulative outcome elements.

Turning now to FIG. 15, an example patient timeline GUI 1500 that includes a plurality of predicted outcome elements within a time aligned graph 1502 is shown. The patient timeline GUI 1500 includes a clinical decision support GUI 1506, similar to the patient timeline GUIs 800, 900, 1000, 1100, 1200 and 1400 described above. Patient timeline GUI 1500 may be displayed on a display device of a care provider device (e.g., user device 134 of FIG. 1) or other user device coupled to a patient information system (e.g., patient information system 100 of FIG. 1). The clinical decision support GUI 1506 may be displayed as a side panel of or other pop-up window on top of the patient timeline GUI 1500. Patient timeline GUI 1500 may be configured as patient-oriented or clinician-oriented, as previously described.

The time aligned graph 1502 may comprise a plot 1504. The plot 1504 may comprise a plurality of data points according to date and status of a chosen parameter plotted within the time aligned graph 1502, similar to as previously described. While FIG. 15 shows only one time aligned graph, it should be understood that more than one time aligned graph may be included in the patient timeline GUI 1500, each plotting a different parameter.

The clinical decision support GUI 1506 may be displayed as a pop-up window, side panel, or other of the patient timeline GUI 1500, as previously described. The clinical decision support GUI 1506 may comprise one or more activity items detailing various determined activity recommendations. Pending activity recommendations may be displayed as items within a pending tab and accepted activity recommendations may be displayed as items within a care plan tab. The one or more activity items may comprise a first activity item 1508 and a second activity item 1512. The first activity item 1508 as displayed within the clinical decision support GUI 1506 may include a first outcome prediction element 1510. The second activity item 1512 as displayed within the clinical decision support GUI 1506 may include a second outcome prediction element 1514. The clinical decision support GUI 1506 may further include a cumulative outcome prediction element 1530.

The first outcome prediction element 1510, when toggled on or otherwise selected, may trigger identification of one or more first algorithms, generation of a first predicted outcome corresponding to the first activity item 1508, and display of a first predicted outcome element 1516 within the time aligned graph 1502 that corresponds to the first predicted outcome. The second outcome prediction element 1514, when toggled on or otherwise selected, may trigger identification of one or more second algorithms, generation of a second predicted outcome corresponding to the first activity item, and display of a second predicted outcome element 1518 within the time aligned graph 1502 that corresponds to the second predicted outcome. The cumulative outcome prediction element 1530, when toggled on or otherwise selected via user input, may trigger identification of one or more third algorithms, generation of a third predicted outcome corresponding to a cumulative activity including both the first activity item 1508 and the second activity item 1512, and display of a third predicted outcome element 1520 that corresponds to the third predicted outcome within the time aligned graph 1502.

Similar to as described with respect to FIG. 14, each of the predicted outcome elements included in the time aligned graph 1402 may include prediction windows indicating a range of possible outcomes and a predicted data point that indicates the most likely outcome. In some examples, the ranges of possible outcomes may overlap such that the prediction windows overlap within the limited display window of the patient timeline GUI 1500. As an example, the first predicted outcome, as demonstrated by the first predicted outcome element 1516, may indicate a worsening of the status of the plotted parameter (e.g., left ventricular ejection fraction) as a result of the first activity item 1508. The second predicted outcome, as demonstrated by the second predicted outcome element 1518, may indicate a first amount of improvement of the status of the plotted parameter as a result of the second activity item 1512. The third predicted outcome, as demonstrated by the third predicted outcome element 1520, may indicate a second amount of improvement of the status of the plotted parameter as a result of both the first and second activity items.

In some examples, the range of potential outcomes for the third predicted outcome may be greater than the range of potential outcomes for either of the first and second predicted outcomes. In this way, the third predicted outcome element 1520 may indicate to the user that the combination of the first and second activity items may result in more improvement of the status of the plotted parameter than the second activity item alone but may also result in less improvement of the status of the plotted parameter than the second activity item alone. In this way, display of the first, second, and third predicted outcome elements within the same time aligned graph may allow the user to visualize the potential outcomes of the various scenarios in a comparative manner alongside the existing patient data and timeline of events. This may increase efficiency and speed of clinical decision making for the user as time spent in review of patient data, determining possible courses of action, and assessing potential outcomes of various courses of action comparatively may be reduced.

Overall, the patient timeline GUI, as herein described by way of example, may present patient data in a longitudinal manner, generate activity recommendations based on the patient data, and may display predicted outcomes and/or projected trends based on selected activities. Multiple predicted outcomes and/or projected trends may be displayed within the limited display window of the timeline GUI, including overlapping elements when predicted outcomes overlap, so as to allow the user to visualize potential outcomes comparatively, thereby increasing efficiency of clinical decision making. In this way, time spent in searching for relevant patient information, determining possible treatments, screenings, and/or interventions, and determining which treatment, screening, and/or intervention to recommend is reduced. Further, in some examples such as for the clinician-oriented patient timeline GUI, the patient timeline GUI may present various sources/algorithms for recommended activities and/or predicted outcomes, allowing the user (e.g., a clinician) to more efficiently analyze the presented recommendations and predicted outcomes. The predicted outcomes may be based on individual activity items, a group of activity items in a cumulative manner, or a group of activity items with selected time designations of occurrence, thus allowing the user to more efficiently determine potential outcomes of various scenarios of treatments/interventions/screenings/etc.

The technical effect of presenting patient data in a patient timeline GUI with predicted outcomes based on one or more potential interventions as disclosed herein is that user/clinician time spent searching for relevant patient data may be reduced and inaccurate care plans due to missing or overlooked patient data may be mitigated, while also decreasing network traffic and/or reducing processing demands by reducing the number of user interactions with various interface (e.g., to look up and visualize patient data). When the patient timeline GUI and/or the clinical decision support GUI are displayed and when the additional display elements (e.g., the various pop-up windows described herein) are displayed, the one or more data repositories (e.g., EMRs, PACS, ECG management systems, etc.) may exist in an un-launched state (e.g., not displayed and not currently accessed by the display device.) In this way, the data from the data repositories may be used to generate medical history event elements and activity recommendations that may be displayed as activity items within the clinical decision support GUI.

Displayed predictive data, such as predicted outcomes and/or projected trends, within the patient timeline GUI may further reduce time spent by the user in determination of activities to perform. As the algorithms may incorporate the patient data, which may include most recent data points, prior trends and/or results to interventions, the predicted outcomes/projected trends may more efficiently determine a potential result of an intervention than would be possible with manual evaluation of the data in consideration with an activity or group of activities. Further, determining which algorithm to use to determine predicted outcomes via a rules module may reduce processing power in attempting to determine predicted outcomes with less than ideal algorithms.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects. This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A computing device comprising a display screen, the computing device configured to display on the display screen a menu listing one or more electronic medical records (EMRs) of one or more patients, and additionally being configured to display on the display screen a patient timeline graphical user interface (GUI) accessible from the menu, wherein the patient timeline GUI displays, for each patient, patient data as longitudinal medical history events and one or more predicted outcome elements of one or more corresponding parameters of a plurality of parameters of the patient data, the patient data obtained from the one or more EMRs and the one or more predicted outcome elements generated based at least in part on the patient data, wherein each element of the longitudinal medical history events and the one or more predicted outcome elements is selectable to launch a pop-up window with additional information related to the selected element, wherein the patient timeline GUI is displayed while the one or more EMRs are in an unlaunched state, wherein the patient timeline GUI further comprises an event history panel including a plurality of event types, each event type of the plurality of event types including one or more event icons arranged chronologically according to a timeline, wherein the one or more event icons each indicate that an event of a corresponding event type occurred at a corresponding time according to the timeline, wherein the event history panel is time aligned with one or more time aligned graphs of patient data parameters displaying one or more predicted outcome elements for corresponding patient data parameters, wherein the plurality of event types includes at least two of: exams, procedures, encounters, hospitalizations, and disease events, wherein the patient timeline GUI includes a decision support element, the decision support element being selectable to launch a clinical decision support GUI, the clinical decision support GUI being a modification of the patient timeline GUI, wherein the clinical decision support GUI is displayed as a side panel of the patient timeline GUI, wherein the clinical decision support GUI comprises a plurality of selectable elements, including an outcome prediction element, an accept element, and a cancel element, wherein the outcome prediction element, when selected for a first activity, triggers generation of predicted outcomes for one or more parameters of the patient data based on the first activity, wherein the accept element, when selected for the first activity, triggers inclusion of the first activity to a care plan, and wherein the cancel element, when selected for a second activity, triggers exclusion of the second activity from the care plan.

2. The computing device of claim 1, wherein the patient data is segmented into the plurality of parameters and each of the plurality of parameters is further segmented into the plurality of event types.

3. The computing device of claim 2, wherein each of the plurality of parameters is displayed in a separate time aligned graph of the one or more time aligned graphs, wherein each time aligned graph displays a respective predicted outcome element corresponding to a parameter displayed within the time aligned graph.

4. The computing device of claim 1, wherein the clinical decision support GUI displays, for each patient, one or more activity recommendations as activity items, the one or more activity recommendations being assigned based on the patient data and a first set of rules.

5. The computing device of claim 4, wherein the one or more predicted outcome elements are displayed within the patient timeline GUI in response to selection of one or more activity items within the clinical decision support GUI.

6. The computing device of claim 5, wherein the one or more predicted outcome elements are generated by one or more artificial intelligence (AI) algorithms based on the one or more activity items and the patient data.

7. The computing device of claim 6, wherein the one or more AI algorithms are determined based on a second set of rules.

8. The computing device of claim 4, wherein the one or more activity recommendations comprise recommendations for at least one of future care, future treatment, future intervention, and future screening.

9. A method for a longitudinal timeline and predictive clinical decision support system, comprising:

displaying a menu listing one or more options for retrieving data of one or more patients from a plurality of data repositories of a hospital, the plurality of data repositories including one or more electronic medical record (EMR) systems;

displaying a patient timeline graphical user interface (GUI) that displays, for each patient, a plurality of elements indicating a plurality of history events determined from the retrieved data from the one or more EMR systems, the plurality of elements being arranged chronologically, wherein one or more elements of the plurality of elements is selectable to launch a pop-up window with additional information related to the selected element;

in response to selection of an element of the plurality of elements, modifying the patient timeline GUI to display a clinical decision support GUI that displays one or more activity items, wherein the patient timeline GUI is displayed while the one or more EMR systems are in an unlaunched state;

in response to selection of one or more of the one or more activity items, generating predicted outcomes of one or more parameters of the data based on the one or more activity items; and displaying the predicted outcomes as predicted outcome elements within the patient timeline GUI, wherein one or more of the predicted outcome elements are selectable to launch a pop-up window with additional information related to a corresponding predicted outcome, wherein the patient timeline GUI comprises a time aligned graph including a plurality of time aligned plots therein, each time aligned plot of the plurality of time aligned plots corresponding to a different parameter of the one or more parameters, wherein the predicted outcome elements are displayed for each of the plurality of time aligned plots at the same time within the time aligned graph, and wherein the predicted outcome elements are displayed while the one or more EMR systems remain in the unlaunched state, wherein the clinical decision support GUI comprises a plurality of selectable elements, including an outcome prediction element, an accept element, and a cancel element, wherein the outcome prediction element, when selected for a first activity, triggers generation of predicted outcomes for one or more parameters of the patient data based on the first activity, wherein the accept element, when selected for the first activity, triggers inclusion of the first activity to a care plan, and wherein the cancel element, when selected for a second activity, triggers exclusion of the second activity from the care plan.

10. The method of claim 9, wherein the predicted outcomes of the one or more parameters are generated based on one or more artificial intelligence (AI) algorithms, wherein the one or more AI algorithms are determined based on a second set of rules applied to the data and the one or more activity items.

11. The method of claim 9, wherein the predicted outcomes of a first parameter comprise a first predicted outcome of a no action condition and one or more second predicted outcome of the one or more activity items, wherein predicted outcomes are generated for the one or more activity items in one or more of an independent manner, a cumulative manner, and a time designated manner.

12. The method of claim 9, further comprising displaying within the patient timeline GUI two or more of a first predicted outcome element for each of the one or more activity items, a second predicted outcome element for a no action condition, a third predicted outcome element for a cumulative condition, and a fourth predicted outcome element for a time designated condition, wherein the two or more are displayed within the same time aligned graph at the same time in an overlapping manner.

13. The method of claim 9, wherein each of the predicted outcome elements is displayed with a respective color corresponding to a status of a trend of a corresponding predicted outcome.

14. A longitudinal patient history timeline system, comprising:

one or more processors; and memory storing instructions executable by the one or more processors to:

output, for display on a display device, a patient timeline graphical user interface (GUI) that includes, for a patient, a plurality of time aligned graphs indicating patient history events, wherein each graph is generated by applying a set of rules to a set of patient data obtained from an electronic medical record (EMR) database;

display within a modification of the patient timeline GUI, an activity recommendation indicating a suggested care measure based on the set of patient data, wherein the modification of the patient timeline GUI comprises a clinical decision support GUI displayed as a side panel of the patient timeline GUI, wherein the clinical decision support GUI displays the activity recommendation as an activity item in an expanded state, and wherein the activity item in the expanded state includes a textual description of a reasoning for the activity recommendation, the textual description identifying one or more criteria from the set of patient data that triggered the activity recommendation based on the first set of rules;

generate predicted outcomes of one or more parameters of the set of patient data based at least in part on the suggested care measure; and display, within one or more of the plurality of time aligned graphs, predicted outcome elements corresponding to the predicted outcomes for each of one or more corresponding parameters, wherein each predicted outcome element is selectable to launch a pop-up window displaying additional information relating to a predicted outcome represented by the selected predicted outcome element, and wherein the patient timeline GUI and the clinical decision support GUI are displayed while the EMR database is in an unlaunched state, wherein the clinical decision support GUI comprises a plurality of selectable elements, including an outcome prediction element, an accept element, and a cancel element, wherein the outcome prediction element, when selected for a first activity, triggers generation of predicted outcomes for one or more parameters of the patient data based on the first activity, wherein the accept element, when selected for the first activity, triggers inclusion of the first activity to a care plan, and wherein the cancel element, when selected for a second activity, triggers exclusion of the second activity from the care plan.

15. The longitudinal patient history timeline system of claim 14, wherein the predicted outcomes of the one or more parameters is generated based on a first suggested care measure and a second suggested care measure.

16. The longitudinal patient history timeline system of claim 15, wherein the first and second suggested care measures are considered in a cumulative manner when generating the predicted outcomes of the one or more parameters.

17. The longitudinal patient history timeline system of claim 15, wherein the first and second suggested care measures are considered in a time aligned manner when generating the predicted outcomes of the one or more parameters.

18. The method of claim 9, wherein each predicted outcome element comprises a predicted data point and a prediction window indicating a range of possible outcomes.

* * * * *